United States Patent
Gordon et al.

(10) Patent No.: US 6,406,876 B1
(45) Date of Patent: Jun. 18, 2002

(54) IMMOBILIZED ENZYMES BIOSENSORS FOR CHEMICAL TOXINS

(75) Inventors: Richard K. Gordon; Bhupendra P. Doctor, both of Potomac, MD (US); Ashima Saxena, Fairfax, VA (US); Shawn R. Feaster, Damascus, MD (US); Donald Maxwell, Baltimore, MD (US); Michelle Ross, Edgewood, MD (US); David Lenz, Bel Air, MD (US); Keith LeJeune, Pittsburgh; Alan Russell, Wexford, both of PA (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/558,511

(22) Filed: Apr. 26, 2000

(51) Int. Cl.[7] .......................... C12Q 1/46; C12Q 1/44; C12Q 1/28; C12Q 1/26

(52) U.S. Cl. .......................... 435/20; 435/19; 435/28; 435/18; 435/25; 435/289.1; 435/283.1; 435/287.1; 435/286.5; 435/963; 435/970

(58) Field of Search .......................... 435/20, 19, 28, 435/18, 25, 289.1, 283.1, 287.1, 286.5, 963, 970

(56) References Cited

U.S. PATENT DOCUMENTS

| | | | |
|---|---|---|---|
| 4,083,692 A | * | 4/1978 | Epstein et al. ............... 435/20 |
| 4,324,858 A | * | 4/1982 | Goodson et al. ............. 435/20 |
| 4,411,989 A | | 10/1983 | Grow ........................... 435/20 |
| 4,677,019 A | | 6/1987 | Von Bluecher ............... 435/20 |
| 5,001,048 A | | 3/1991 | Taylor et al. ................. 435/4 |
| 5,192,507 A | | 3/1993 | Taylor et al. ................. 435/174 |

FOREIGN PATENT DOCUMENTS

WO  WO 87 00914 A  2/1987

OTHER PUBLICATIONS

Russell, 1995 "Biocatalytic Nerve Agent Decontamination with Protein–Polymers" Univ. Pittsburgh Proposal to USAMRMC.

"Reactivation of Various OP Inhibited Immobilized (Sponge) FBS–AchE with HI–6" Table of data. Fax from Doctor, Dec. 21, 1995.

"Abstract: Covalent Linkage of Mammalian Cholinsterases and OP Hydrolyzing Enzymes Within Polyurethane Foams" Fax from Doctor to Russell Feb. 27, 1996 and fax from Madeya to Russell, Feb. 28, 1996.

Russell, Jun. 4, 1996 "White Paper: Biotechnology Versus Chemical Weapons: A Battle for the 21st Century. The Use of Stabilized Enzymes to Decontaminate and Demilitarize".

LeJeune, et al., "Dramatically Stabilized Phosphostriesterase—Polymers for Nerve Agent Degradation" Publication.

"Abstract: Covalent Linkage of Mammalian Cholinesterasee Within Plyurethane Foams" Fax from Doctor to Russell, Jun. 10, 1996. Submitted to the Proceedings of the 1996 Medical Defense Bioscience Review.

"Proceedings of the CB Medical Treatment Symposium: An Exploration of Present Capabilities and Future Requirements", Jul. 7–12, 1996, Spiez, Switzerland.

(List continued on next page.)

Primary Examiner—Louise N. Leary
(74) Attorney, Agent, or Firm—Elizabeth Arwine

(57) ABSTRACT

Methods, compositions and materials useful in the detection of organophosphorous and organosulfur compounds are disclosed. In particular, biosensors wherein a porous or a non-porous support having an enzyme immobilized upon or within are disclosed. The biosensors exhibit enzymatic stability at extreme temperatures and/or denaturing conditions, and similar kinetic characteristics of the soluble form of the enzymes utilized. The enzyme does not leach from the porous or non-porous support and the material retains enzymatic activity after prolonged storage. Differential biosensors are also disclosed.

31 Claims, 31 Drawing Sheets

Modeled surfaces of ChEs and triesterase. The top row shows a view of the front of the enzymes with the lip of the active site gorge outlined with a dotted line in the center. The bottom row shows the backside of the enzymes (180° rotation). The Lysine and Arginine residues on the surface, which are potential coupling sites to the polymer, are shaded dark in both the top and bottom row.

OTHER PUBLICATIONS

"Data Tables regarding polyurethane foam sponges" Fax from Doctor to LeJeune Apr. 17, 1997.

Solicitation DAA 005–97–I–1981, Contractor Russell for Synthesis work. Includes Univ. Pittsburgh data tables regarding synthesis.

Slide, notes indicate that prepared that Sep. 22,1997 and presented Oct. 15, 1997, Univ. Pittsburgh Seminar.

Slide, notes indicate that prepared Sep. 15, 1997 and presented Sep. 19, 1997, W.V.U. Grad Student Symposium.

Slide, notes indicate that prepared Nov. 21, 1996 and presented Apr. 1997, ACS Meeting.

LeJeune, 1997 "Biotechnology versus Chemical Weapons: Implementing Enzyme Technology in Bioremediation" Proposal to Department of Chemical Engineering, Carnegie Mellon Univ.

Russell, Nov. 13, 1997, "Biotechnology versus Chemical Weapons: Implementing Enzyme Technology in Decontamination/Demilitarization" Proposal to Edgewood Research, Development and Engineering Center.

Lejeune, et al., 1999 "Biocatalytic Nerve Agent Detoxification in Fire Fighting Foams" Chemical Abstracts, vol. 130, No. 19.

Braatz, (1994) "Biocompatible Pllyurethane–Based Hydrogel" in Journal of Biomaterials Applications, vol. 9.

Doctor, et al., (1991) "Enzymes as Pretreatment Drugs for Organophosphate Toxicity" Neuroscience & Biobehavioral Reviews, vol. 15, pp. 123–128.

Ember, (1997) "Detoxifying Nerve Agents" Chemical & Engineering News Sep. 15, 1997.

Gordon, et al., (1998) "Exploiting Immobilizing Enzymes: Detoxification of Nerve Agents" Proceedings from the 6th CBW Protection Symposium, Stockholm, Sweden, May 1998.

Gordon et al., "Exploiting Immobilized Enzymes: Detoxification in of Nerve Agents" in the Summary Digest of the 21st Army Science Conference, Jun. 15–17, 1998.

Gordon et al., (1997) "Potential Applications of Immobilized Cholinesterases: Tools for Protection, Decontamination, and Detection" in The ASA Newsletter 97–5, Issue No. 62.

Gordon et al., "Immobilized Enzymes–Selective and Specific Sensors for Organophosphate Chemical Toxins" a Proposal "White Paper" of Walter Reed Army Institute of Research.

Gordon et al., (1990) "Vasoactive Intestinal Polypeptides Induce Guinea–Pig Ileum Contraction by Causing Release of Endogenous Acetylcholine" Arch. Int. Pharmacodvn. 305, pp. 14–24.

Havens et al., (1993) "Reusable Immobilized Enzyme/Polyurethane Sponge for Removal and Detoxification of Localized Organophosphate Pesticide Spills" Ind. Eng. Chem. Research 1993, 32.

LeJeune et al., "Fighting Nerve Agent Chemical Weapons with Enzyme Technology", Ann NY Acad. Sci. (1998) 864:153–170.

LeJeune et al., (1996) "Covalent Binding of a Nerve Agent Hydrolyzing Enzyme Within Polyurethane Foams" in Biotechnology and Bioengineering, vol. 51, pp. 450–457.

LeJeune et al., (1996) "Covalent Linkage of Mammalian Cholinesterases Within Polyurethane Foams" Proceedings from the 1996 Medical Defense Bioscience Review.

Medlin, (1998) "Super Sponges" Environmental Health Perspectives, vol. 106, No. 4, pp. A182–A184.

* cited by examiner

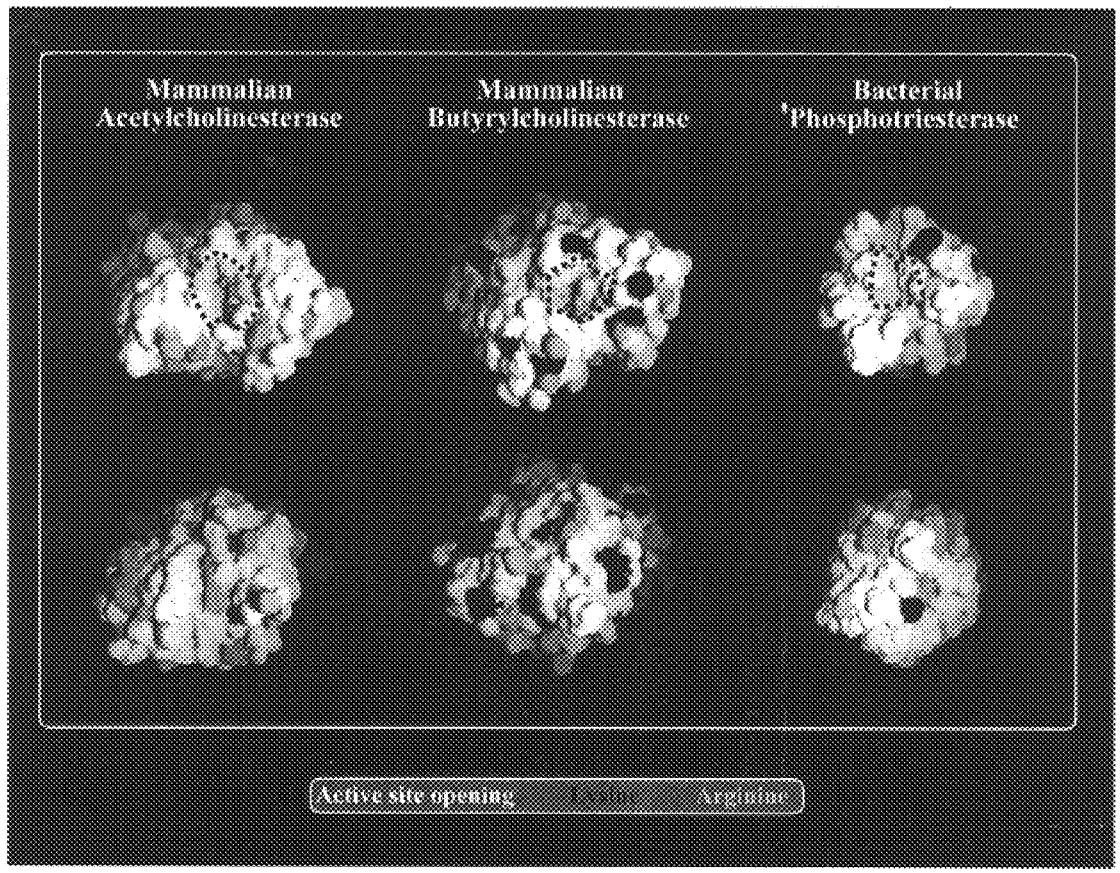

Figure 1A  Modeled surfaces of ChEs and triesterase. The top row shows a view of the front of the enzymes with the lip of the active site gorge outlined with a dotted line in the center. The bottom row shows the backside of the enzymes (180° rotation). The Lysine and Arginine residues on the surface, which are potential coupling sites to the polymer, are shaded dark in both the top and bottom row.

Similarly, a model of the surface of laccase is shown with available residues to couple covalently to the prepolymer (top, front of enzyme; bottom, backside of enzyme).

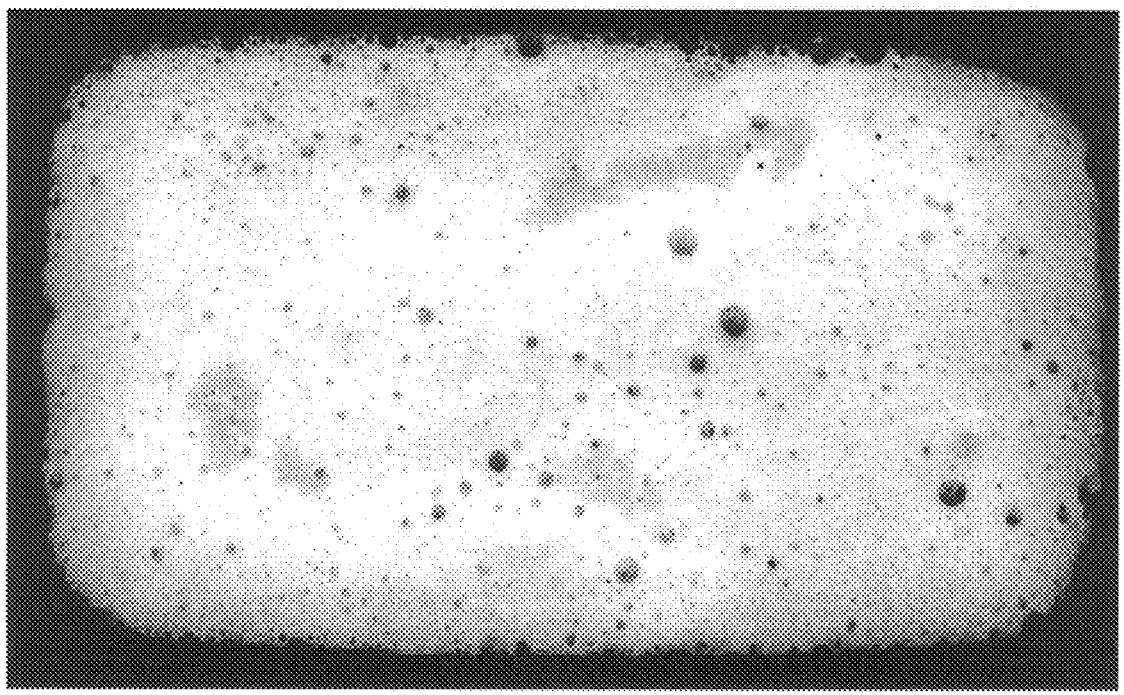
Figure 2. Final product: FBS-AChE sponge

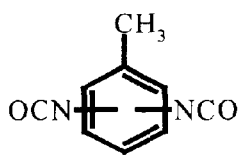
TDI prepolymer functional group
1. Aqueous Initiation of Polymerization
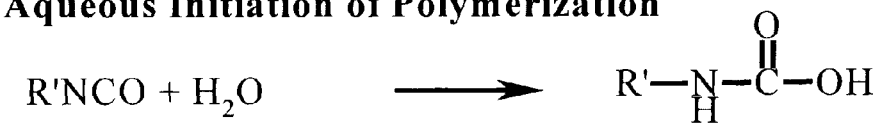
2. Amine Formation and $CO_2$ Evolution (foaming)
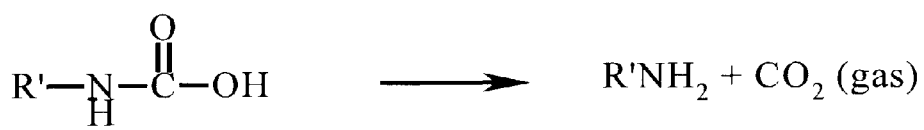
3. Prepolymer Crosslinking
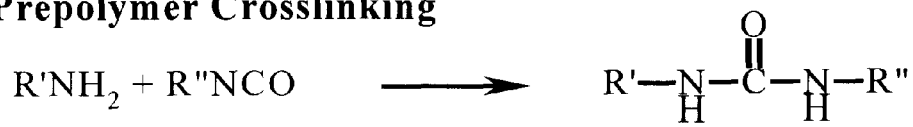
4. Covalent ChE Incorporation at Aliphatic Amino Group(s)
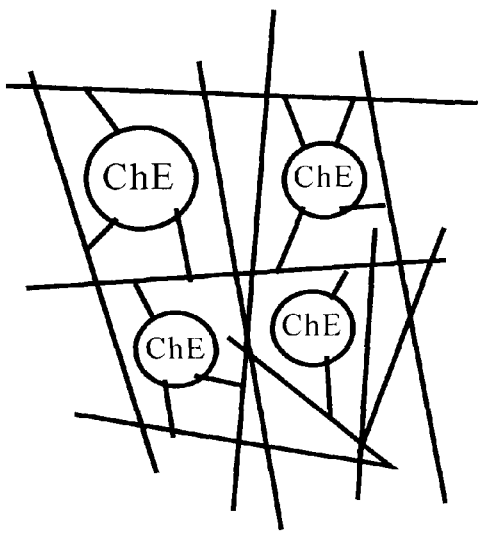
polyurethane crosslinked ChE
Figure 3

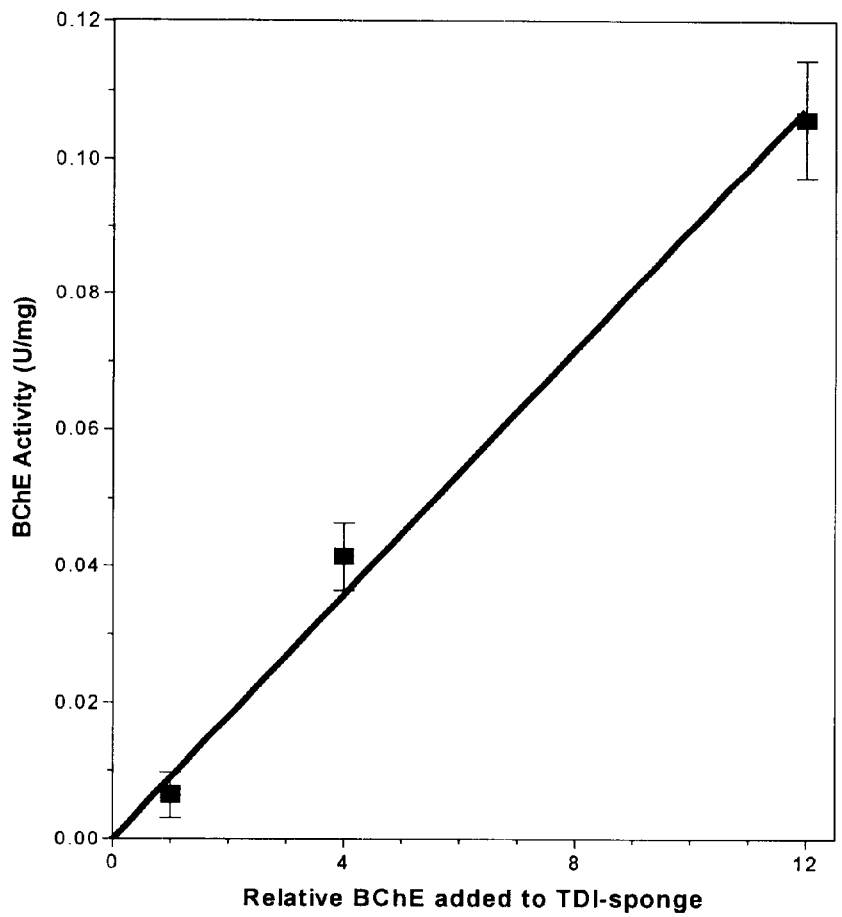
Figure 4. A linear correlation was observed between the amount of BChE added to the prepolymer during synthesis and the amount of BChE activity observed in the final sponge.

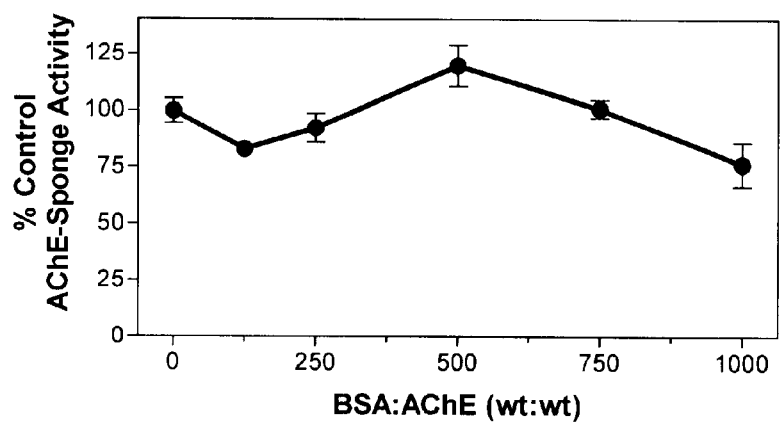
Figure 5. Increasing amounts of BSA were added during synthesis to a constant amount of AChE and TDI polymer

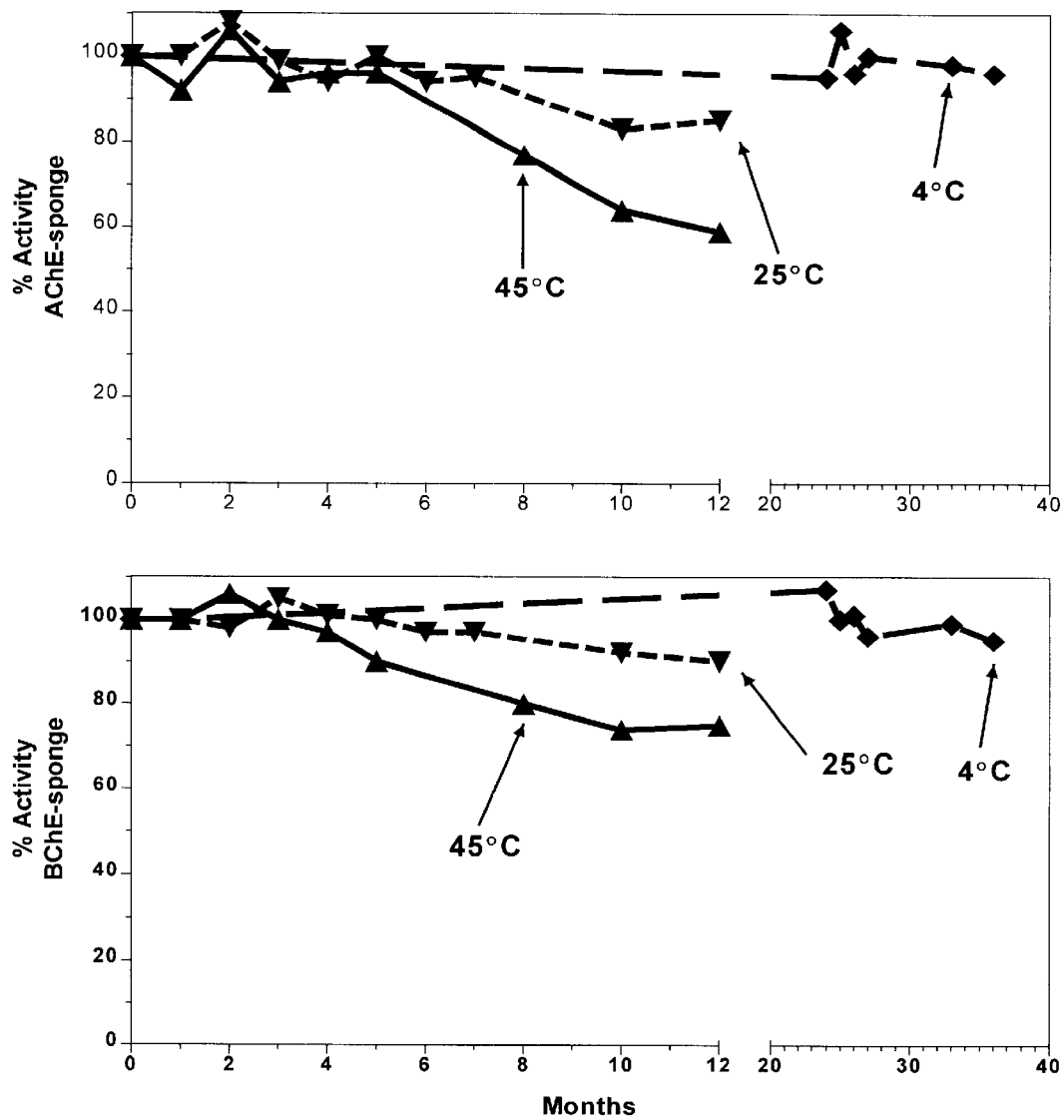
Figure 6. Stability of AChE (top) and BChE (bottom) sponges at various temperatures.

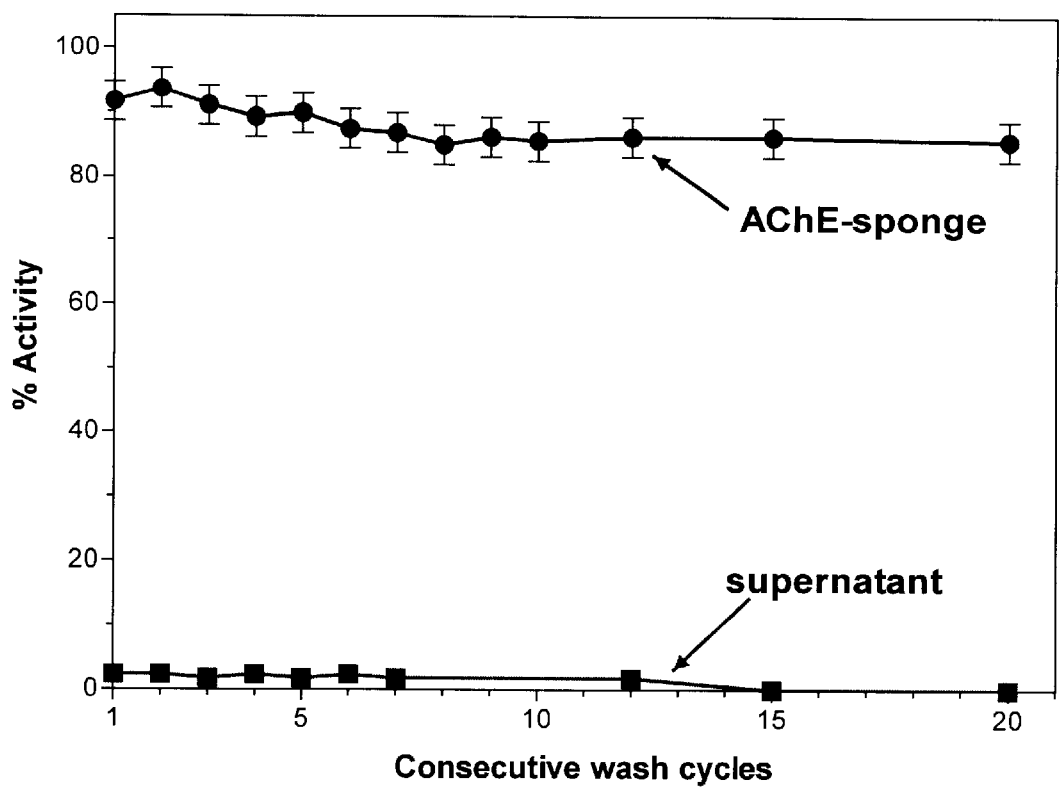
Figure 7. An AChE-sponge was alternately washed with phosphate buffer and assayed for activity. This procedure was carried out for three days. Similar results were observed for BChE-sponge.

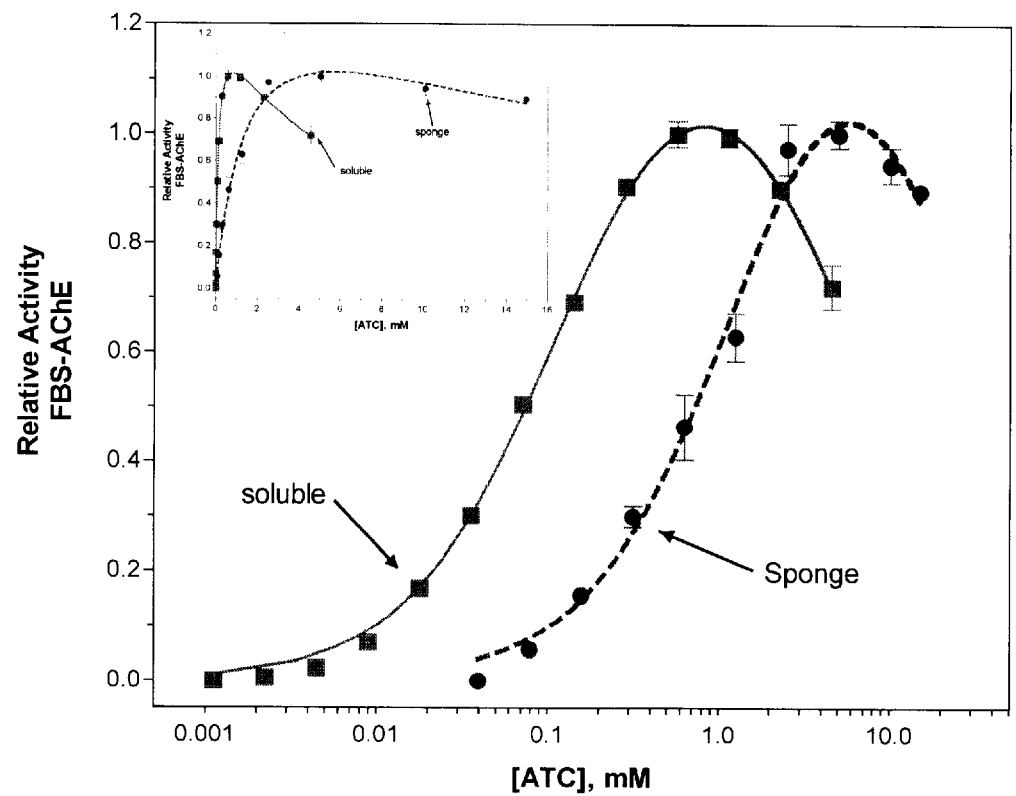
Figure 8. Substrate concentration dependent curve for soluble and polyurethane coupled AChE.

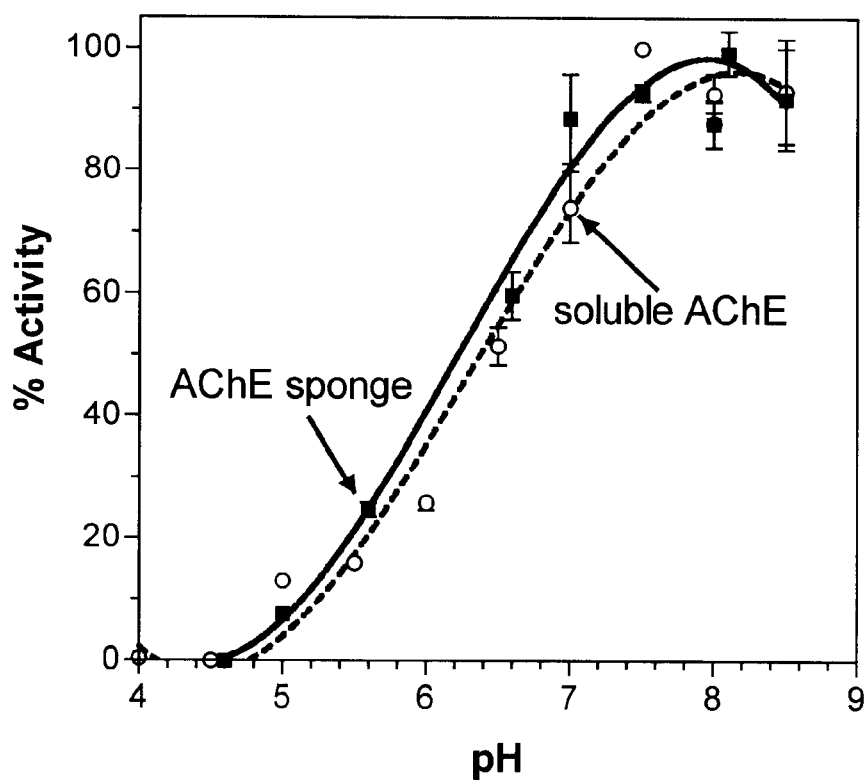
Figure 9. pH profile of soluble and immobilized acetylcholinesterase

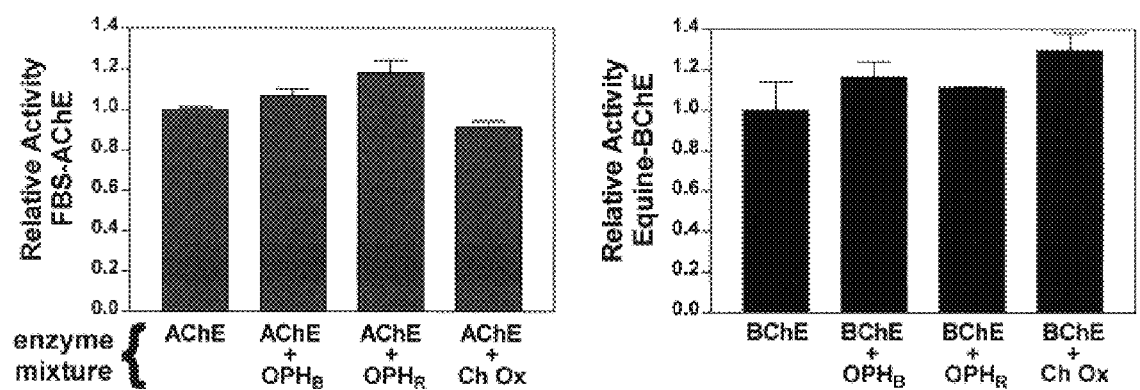
Figure 10. Co-immobilization of ChEs and OP hydrolases.

Figure 11A shows a version of a manual mixing gun and Figure 11B shows a disposable mixing stator. Complete mixing of the enzyme in aqueous solution and the viscous prepolymer is accomplished in the stator. The product shown here for illustrative purposes is green, while the two starting components are yellow and blue.

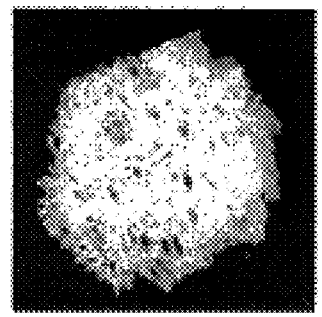
Figure 12. A small sponge about 3/8" in diameter containing AChE immobilized to the polyurethane.

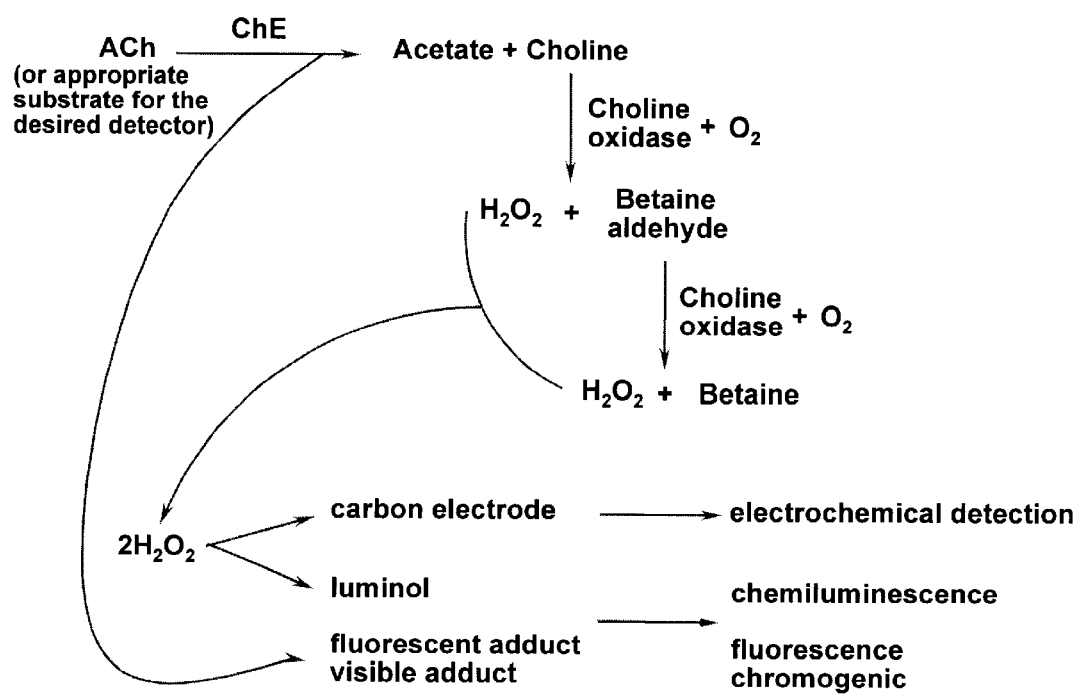
Figure 13A  Alternate schemes for detecting cholinesterase activity in the biosensor. This figure shows a variety of possible detection methods, such as qualitative colorimetric changes, chemiluminescent for a dark environment, and additional amplification by coupling the ChE reaction to choline oxidase.

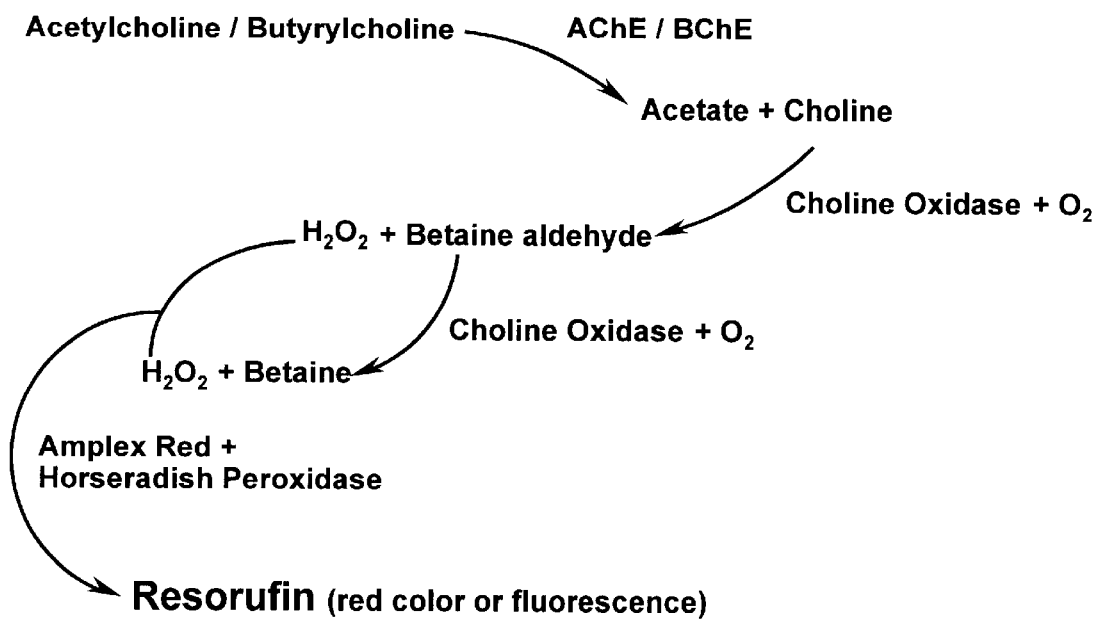
Figure 13B. Amplex Red visual and fluorometric pathway

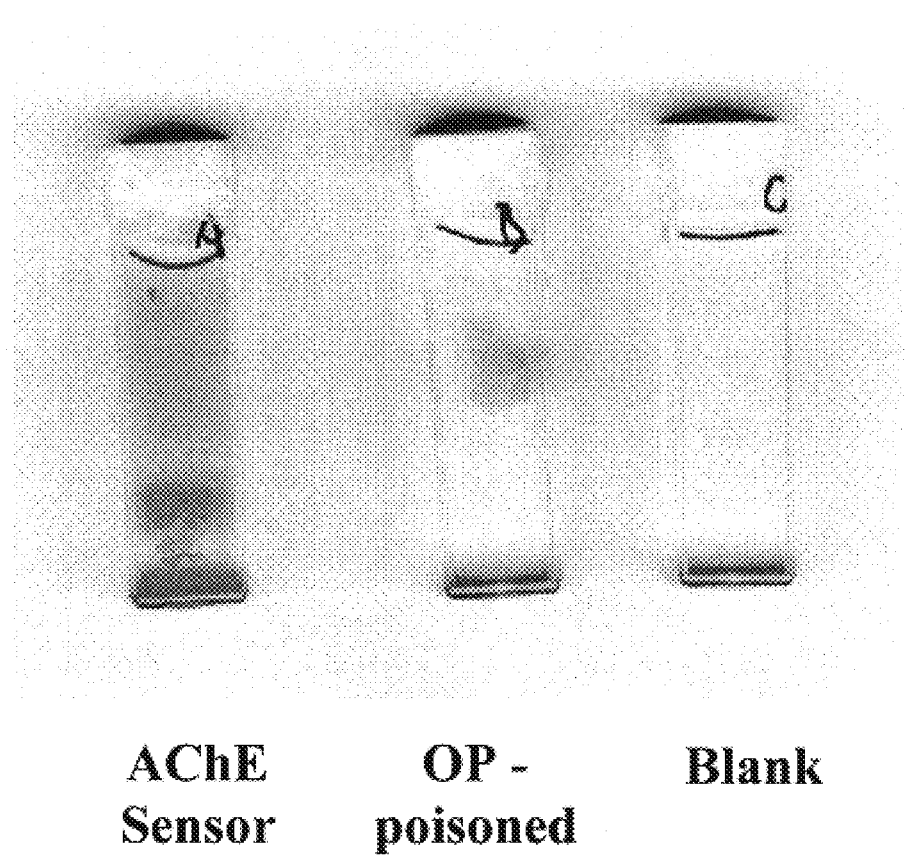
Figure 13C. AChE and Choline oxidase Biosensor reaction to the OP MEPQ

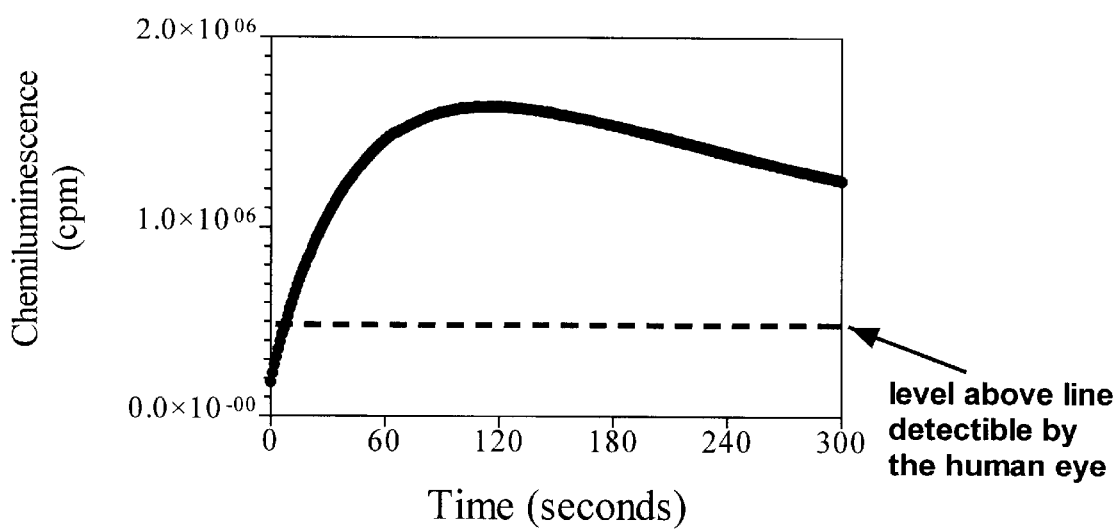
Figure 13D. Chemiluminescence of AChE/Choline oxidase sensor

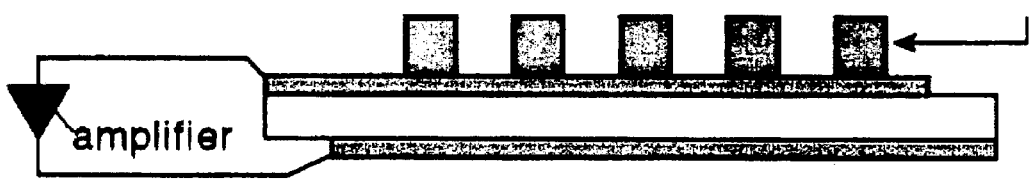
Figure 14. Model of a carbon electrode with immobilized cholinesterase enzyme.

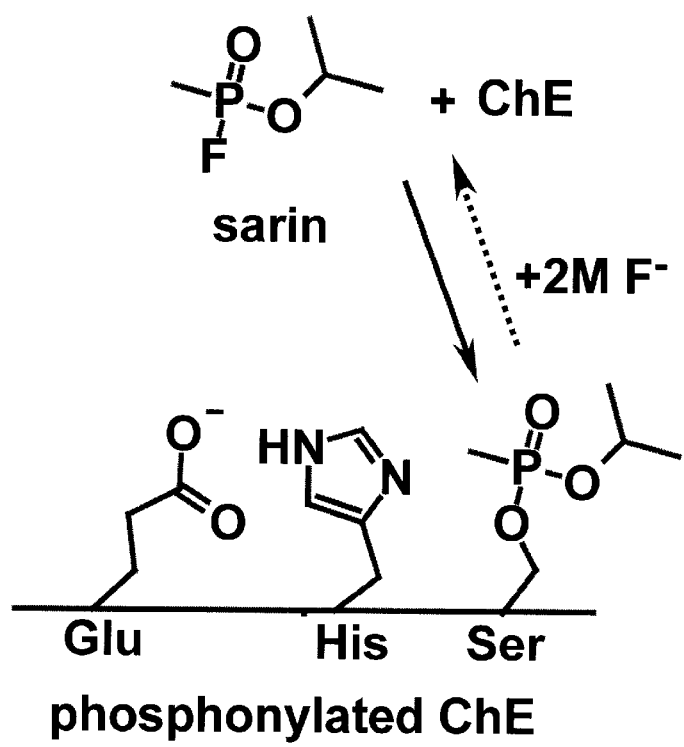
Figure 15. Using high fluoride ion concentrations to reverse the reaction between the OP and ChE. This reaction will permit the determination of the type of OP bound to the badge.

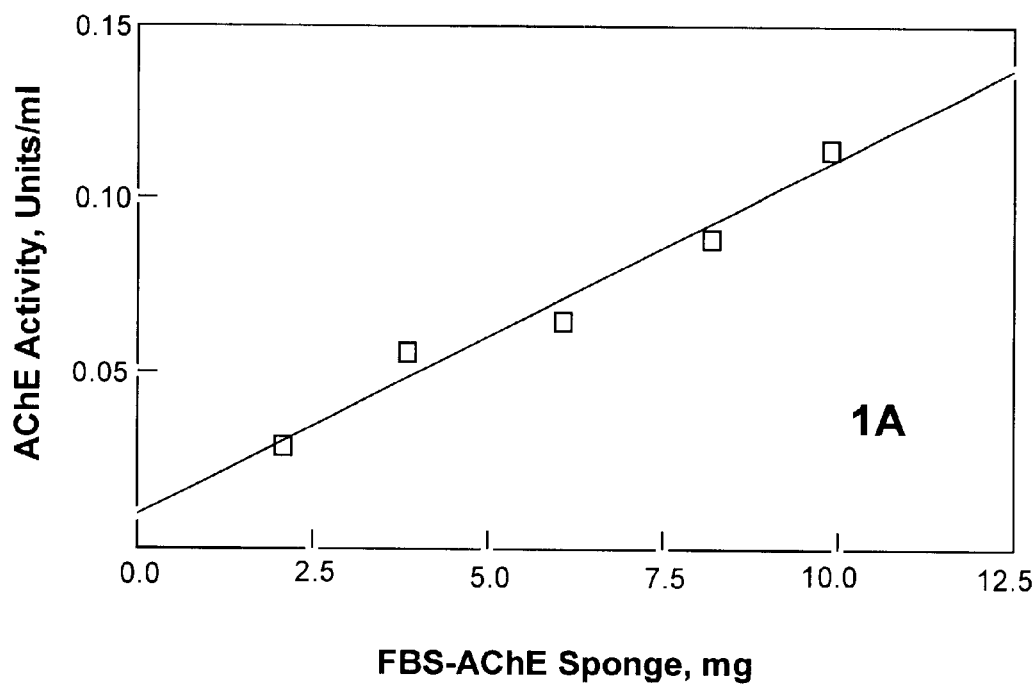
Figure 16 A. Enzyme activity of immobilized FBS-AChE.
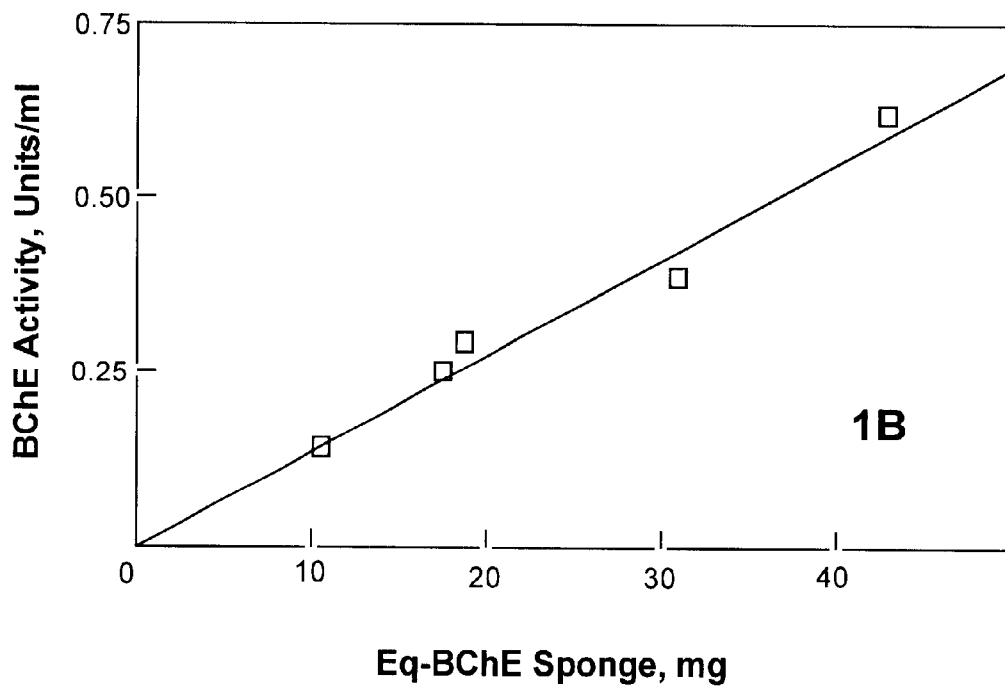
Figure 16 B. Enzyme activity of immobilized Eq-BChE.

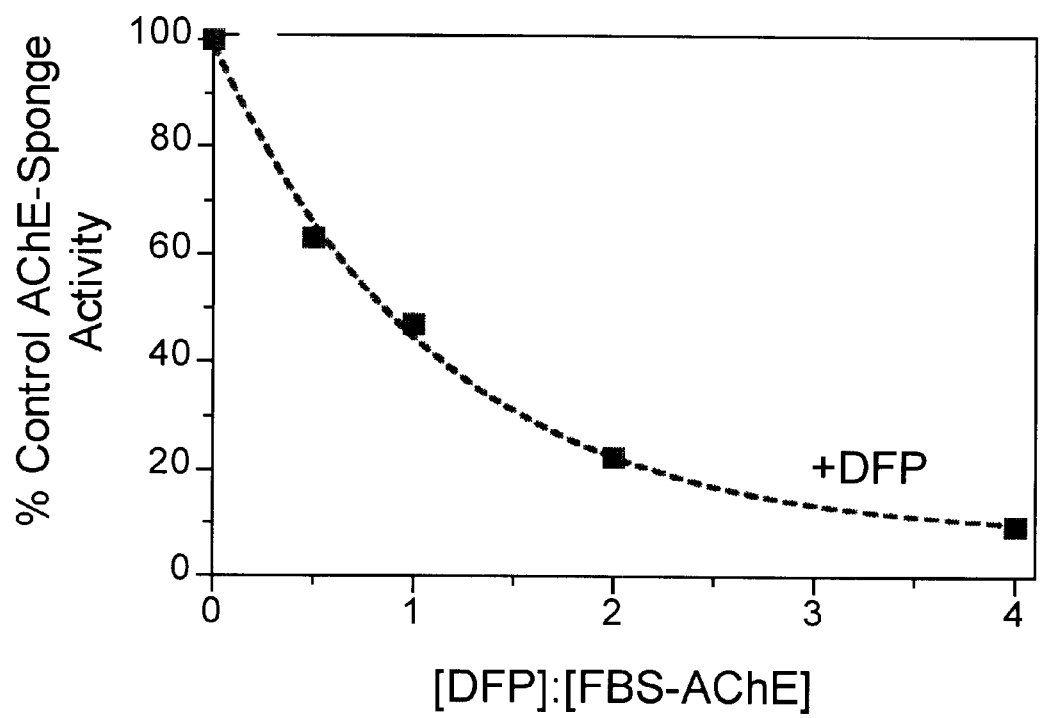
Figure 17. Inhibition of foam-immobilized FBS-AChE by DFP.

Figure 18. Inhibition of foam-immobilized Eq-BChE by DFP.

The pH profile of soluble and immobilized choline oxidase.

Substrate concentration dependent curve for soluble and polyurethane coupled choline oxidase.

IMMOBILIZED ENZYMES BIOSENSORS FOR CHEMICAL TOXINS

TECHNICAL FIELD

This invention relates generally to the field of detecting hazardous chemicals. More particularly, the present invention relates to methods, compositions, devices and kits thereof useful in the detection of chemical warfare agents and insecticides.

BACKGROUND OF THE INVENTION

Organophosphorus and organosulfur (OP refers to both types) compounds, are used extensively in insecticides and are highly toxic to many organisms including humans. Insecticide residues are found in soil and groundwater, and the detection of these residues is important for their elimination from the environment and to protect the health of both humans and animals. OP compounds are also used in nerve agents, such as sarin, phosphine, soman, and tabun, for chemical warfare purposes.

These agents are some of the most potent toxic agents and are specific inhibitors of acetylcholinesterase (AChE). The sequel to AChE poisoning is a cholinergic crisis in man; the clinical effects are directly related to acetylcholine accumulation. Nerve agents are classified into G agents (GD, soman; GB, sarin; and GA, tabun) and the V agents (VX). These agents differ in physical properties, for example, VX has a much lower vapor pressure than the G agents. However, the toxicity and main effects of the agents are very similar—inhibition of acetylcholinesterase and subsequent breakdown of the normal operation of the automatic and central nervous systems. Thus, detection of organophosphorous compounds is of paramount importance to prevent casualties due to OP exposure.

The need for the reliable determination of these cholinesterase inhibitors has led to the development of a number of sophisticated instrumental methods, mostly involving the use of gas and liquid chromatography and mass spectrometry. Also a number of liquid phase chemiluminescence procedures have been developed for the determination of inorganic and organic species mostly utilizing the luminol and peroxyoxalate reactions. See Robards K. and Worsfold P. J., (1992) Anal. Chem. Acta, 266:147.

These traditional methods are not practical for individual use as the methods are time consuming and complicated and the instruments utilized are expensive, non-portable and require high maintenance. Additionally, the measurement of nerve agents in mixtures with these traditional methods requires cumbersome extraction and manipulation procedures.

Thus, biosensors were developed as an alternative to the traditional gas and liquid chromatography and mass spectrometry technology. Generally, biosensors include those which are enzyme-based and bioaffinity-based. An enzymatic biosensor uses an enzymatic or metabolic process to detect a reaction product which occurs between an incoming substrate and an immobilized enzyme. A bioaffinity sensor relies on a biological binding event of a target substance.

The prior art biosensors are electronic devices which produce electronic signals as the result of biological interactions. These biosensors comprise a biological receptor linked to an electronic transducer in such a way that biochemical activity is converted into electrical activity. The electronic component of the biosensors measure voltage, amperage, wavelengths, temperature, or mass. See Lowe, C. R. (1984) Biosensors 1:3–16.

Biosensors are widely used to detect biological, pharmacological, or clinically important compounds. Generally, enzyme biosensors are selective, sensitive and specific. They are portable, simple and easy to use. Enzymatic biosensors can detect only those substances of interest and ignore all other environmental and biological interference.

Various cholinesterases (ChEs) biosensors have been described. These biosensors comprise ChEs non-covalently immobilized on a support. Cholinesterases have been immobilized on a full gamut of solid and gel supports such as glass, silica, ion-exchange resins, agarose, and nylon supports. Ideally, the preferred methods of immobilizing enzymes on solid supports have high coupling rates and the preferred biosensors retain enzymatic activity and maintain stability. However, biosensors which have non-covalently bound enzymes possess undesirable characteristics such as enzymatic instability at ambient and/or denaturing conditions, a propensity of the enzymes to leach from the surface to which it was non-covalently bound, and a short half-life in solution.

Generally, most methods which covalently bind enzymes to polymers utilize harsh or protein unfriendly conditions diminish enzymatic activity and stability. Although U.S. Pat. No. 4,342,834 discloses a method of making isocyanate-based polyurethane foams wherein enzymes having varying degrees of activity are covalently linked, it does not disclose a material useful for the detection of OP compounds nor does it disclose a method of using the material for the detection of OP compounds.

Furthermore, it does not disclose a method of immobilizing enzymes on a porous support, whereby air induced shear forces are reduced which results in the retention of enzymatic activity.

SUMMARY OF THE INVENTION

In one embodiment the invention relates to a material comprising a porous support wherein an enzyme is immobilized upon or within which material is suitable for use as a biosensor for the detection and measurement of hazardous compounds such as OP compounds.

In a preferred embodiment, the material comprises an enzyme that is covalently bound to a porous support, the immobilized enzyme exhibits enzymatic stability at extreme temperatures and/or denaturing conditions, and similar kinetic characteristics of the soluble form. The enzyme does not leach from the porous support and the material retains enzymatic activity after prolonged storage.

In another embodiment, a plurality of materials comprising a porous support wherein a plurality of enzymes is immobilized upon or within which the plurality of materials is suitable for use as a differential biosensor having multiple zones for detecting the presence of specific OP compounds. In a preferred embodiment, the dimensions of the biosensor are in the range from about 0.25"×0.25"×0.03125" to about 6"×4"×0.25".

Yet another embodiment of the invention relates to methods of making a material comprising a porous support wherein a plurality of enzymes is immobilized which material is suitable for use as a biosensor for detecting hazardous compounds such as OP compounds. Synthesis of the porous support involves the use of a prepolymer such as polyether and a surfactant such as P-65. In a preferred embodiment, the method of making the material reduces air induced shear forces or shear stress which reduce enzymatic activity. During synthesis of the material by prior art methods, for example a mixing drill, the enzymes utilized are subjected to fluid forces or shear stress. Use of a device that gently folds the components into one another greatly reduces these fluid forces or shear stress, and is the preferred device for enzymes, specifically enzymes that are sensitive to the high shear forces of the drill mixing device. The low shear mixing device more than doubles the resultant AChE or BChE immobilized enzyme activity when compared to an identical mixture prepared with the high shear device. Additionally, use of additives such as surface-acting polymers, e.g. P-65, or low concentrations of glycerol protects against enzyme denaturation induced by shear forces.

As disclosed herein, one of ordinary skill in the art may synthesize a variety of porous supports with the various prepolymers and surfactants available.

When immobilized, the enzymes of the biosensors are stable under extreme temperatures and/or denaturing conditions. These enzymes include cholinesterases, choline oxidase, hydrogen peroxidase, organophosphate hydrolase, phosphotriesterase, laccase, and derivatives thereof.

The biosensors are suitable for detecting and quantifying OP chemicals in gases and liquids and on solids. For example, the biosensor may be used to detect OP compounds in water and/or soil. The biosensor may be used to detect OP compounds on natural, synthetic and/or biological surfaces, such as wood, plastic and skin. By using mammalian cholinesterases such as FBS-AChE or Eq-BChE rather than Eel Cholinesterase as is found in the M272 ticket (currently used to detect organophosphate compounds; available from Truetech, Inc.), the immobilized sensor will display the same sensitivity to OPs that mankind is susceptible to now, or any new or novel OPs that might be produced in the future against mankind.

In one embodiment, the biosensor comprises at least one indicator to indicate the presence of an OP compound by fluorescent, chromogenic or chemiluminescent determination.

In another embodiment the biosensor comprises a carbon electrode for the detection of an OP compound by determining cholinesterase activity.

In another embodiment, the amount and source of the various OP compounds may be determined.

Yet another embodiment relates to kits. Kits may include, along with the biosensor, the indicators for both quantitative or qualitative detection of OP compounds and means for transmitting results to a central collection point, e.g. computer, satellite uplinks, radio relays, handheld battery operated measuring devices, etc. For example, one may quantitatively analyze the OP compounds by using a handheld battery operated measuring devices and interfacing with a computer to calculate reaction rates which rates may be relayed to a central collection point. These kits may also contain instructions, solutions and compositions needed for operation. The compositions and solutions may be placed in containers, test tubes, etc.

Other embodiments include the methods of using the instant biosensors for the quantitative or qualitative determination of hazardous compounds such as OP compounds.

DESCRIPTION OF THE DRAWINGS

This invention is further understood by reference to the drawings wherein:

FIG. 1A illustrates the modeled surfaces of acetylcholinesterase, butyrycholinesterase and phosphotriesterase.

FIG. 2 shows a cured material.

FIG. 3 schematically illustrates the specific reaction of the enzymes with prepolymer.

FIG. 4 shows the linear correlation between the amount of BChE added during synthesis of the material and the amount of BChE in the final material.

FIG. 5 shows the increasing amounts of BSA added during synthesis to a constant amount of AChE and TDI polymer.

FIG. 6 illustrates that the materials maintained enzymatic stability for more than 3 years at 4° C. and more than 12 months at 25° C. and 45° C.

FIG. 7 shows that the material maintained enzymatic activity after consecutive washes.

FIG. 8 shows a substrate concentration dependent curve for soluble and polyurethane coupled AChE.

FIG. 9 illustrates the pH range of soluble and immobilized AChE.

FIG. 10 shows the relative activities of co-immobilized ChEs and OPHs.

FIG. 12 shows a small material comprising immobilized AChE.

FIG. 13 schematically illustrates alternate schemes for detecting ChE activity.

FIG. 14 is a model of a carbon electrode with immobilized ChE.

FIG. 15 illustrates how $F^-$ reverses the reaction between an OP compound and ChE.

FIG. 16A illustrates the enzyme activity of immobilized FBS-AChE. FIG. 16B illustrates the enzyme activity of immobilized Eq-BChE.

FIG. 17 represents inhibition of foam-immobilized FBS-AChE by DFP.

FIG. 18 represents inhibition of foam-immobilized Eq-BChE by DFP.

DETAILED DESCRIPTION OF THE INVENTION

Figure 1B:
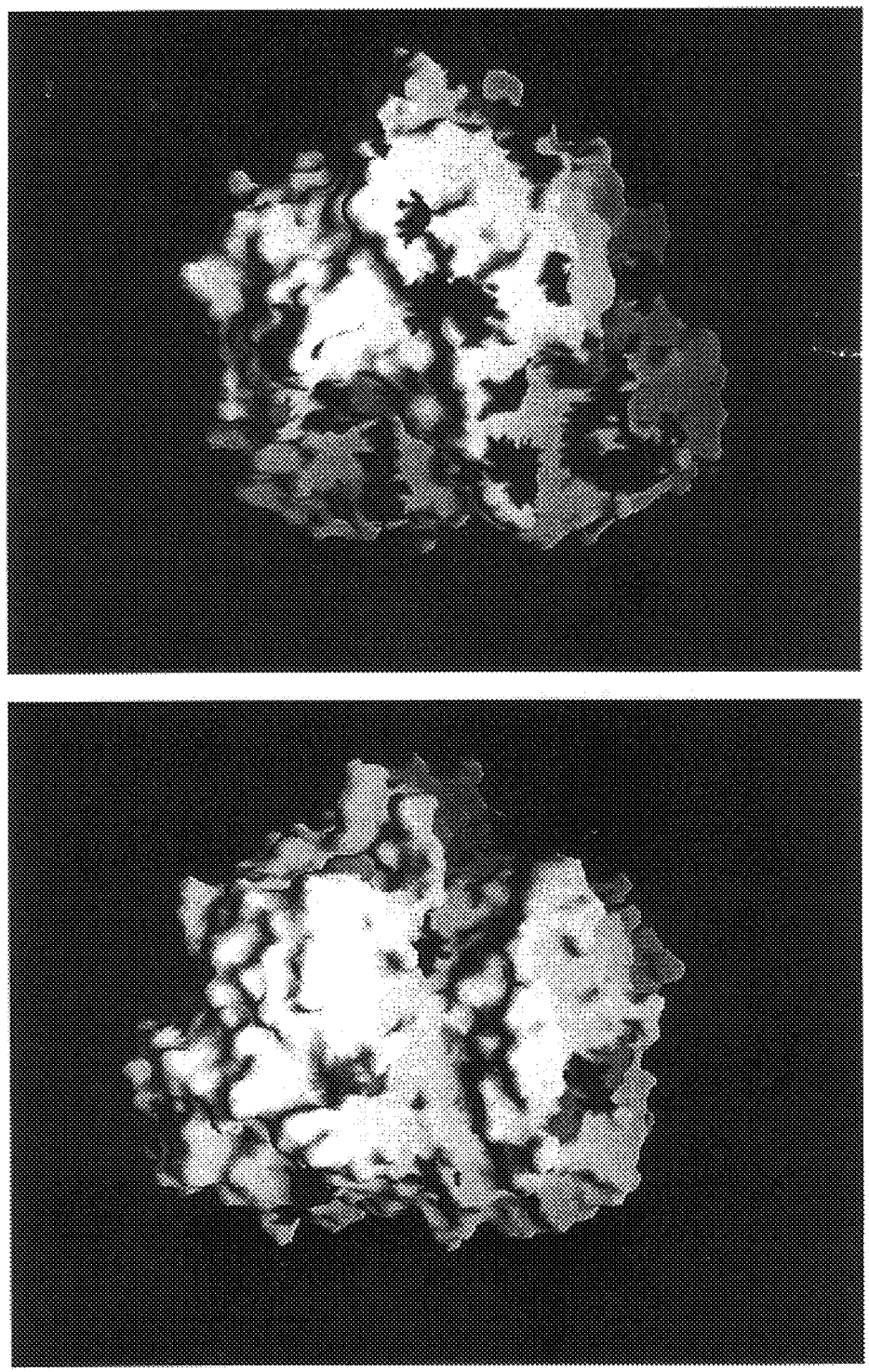
FIG. 1B illustrates a model of the surface of with available residues to couple covalently to the prepolymer (top, front of enzyme; bottom, backside of enzyme).

Enzymes have been incorporated in hypo-based urethane foam during polymer synthesis. See U.S. Pat. No. 4,342,834. Hypoprepolymer is synthesized from a reaction of polyether (or polyester) polyol with isocyanates in the presence of cross-linking agents. See Havens, P. L., et al., *Ind Eng Chem Res* (1993) 32:2254–2258; U.S. Pat. No. 4,137,200; LeJeune, K. E., et al., Biotechnology and Bioengineering (1999) 20;62(6):659–665. Synthesis is initiated by bringing water molecules into contact with isocyanate groups present within the polyurethane prepolymer.

A two-step procedure occurs from this point. Isocyanates react with water to form an unstable carbonic acid, which in turn degrades to an amine yielding $CO_2$ that gives the porous support lift and enables it to rise. The amines readily react with isocyanate groups, leading to production of urea type linkages. Since the enzyme contains multiple functional groups, such as amines and hydroxyls that can react with isocyanates, the enzyme becomes an integral part of the porous support during synthesis. Significant quantities of enzyme can link to the porous support without disrupting the progress of polymer synthesis. The reaction occurring during the polymer synthesis is shown below.

1. $CO_2$ Evolution:

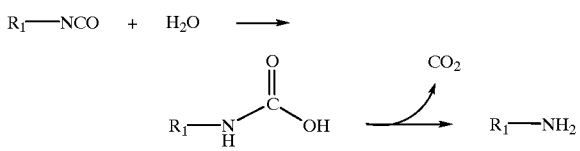

2. Urea Linkage:

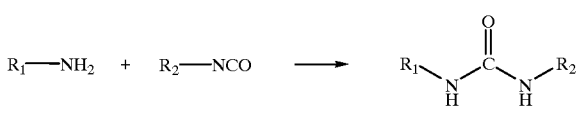

3. Amine Group Enzyme Immobilization:

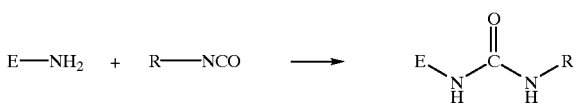

4. Hydroxyl Group Enzyme Immobilization:

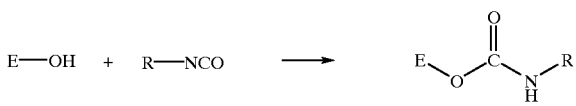

The following list of enzymes (the enzymes can be from a variety of sources, e.g. cell-free, recombinant, etc.) and chemicals are examples of those suitable for use in the instant invention:

OP Sensing Enzymes
Acetylcholinesterase (AChE);
Butyrylcholinesterase (BChE);
Pseudocholinesterase;
Measuring Enzymes
Choline oxidase;
Peroxidase;
OP Differential Detection
Organophosphate hydrolases (OPH);
Phosphotriesterase;
*Pseudomonas diminuta* bacterial OPH (paraoxonase);
Laccases (plus mediators and/or cofactors of laccases, ABTS and analogs thereof);
Diisopropyl fluorophosphate (DFP);
7-(methoxyphosphinyloxy)-1-methylquinolium iodide (MEPQ);
Acetylthiocholine iodide (ATC);
S-butyrylthiocholine iodide (BTC);
5,5'-dithio-bis(2-nitrobenzoic acid) (DTNB);
N,N'-trimethylene bis(pyridinium-4-aldoxime) dibromide (TMB4); and
1-(2-hydroxyiminomethyl- 1-pyridinium)- 1-(4-carboxyaminopyridinium)-dimethylether hydrochloride (HI-6).

In general, the simplest biosensor for OP compounds comprises a material, having ChEs immobilized upon or within a porous support, secured upon a carrier such as plastic, glass, cloth, nylon, rubber, etc. Detection of OP compounds may be qualitatively determined by color. To test for OP compounds, biosensor is exposed to the sample to be tested. Since the inhibition of the immobilized ChE by an OP compound is substantially similar to that observed for the soluble form, only a short duration of exposure to the sample is required. See Table 1.

TABLE 1

| ChE | Enzyme Form | Bimoleclar rate constant ($M^{-1}$ $min^{-1}$) ± SD |
| --- | --- | --- |
| FBS-AChE | soluble | $1.59 \pm 0.52 \times 10^8$ |
|  | coupled to sponge | $1.00 \pm 0.28 \times 10^8$ |
| Equine-BChE | soluble | $4.15 \pm 0.78 \times 10^7$ |
|  | coupled to sponge | $4.21 \pm 2.00 \times 10^7$ |

Time-Dependent Inhibition of ChEs by MEPQ

The material may be washed, squeezed or purified otherwise in order to remove compounds and/or compositions which may cause interference since the immobilized enzyme does not leach out and OP compound is irreversibly bound to the immobilized enzyme. A substrate may be embedded on or in the porous support or applied to the material after exposure to the sample wherein the substrate remains soluble or mobile. An appropriate buffer may be applied to the material. A change in color or luminescence of the material indicates the presence of an OP compound.

These biosensors may be disposed after a single use or may be reused. By reusing the biosensor, the material accumulates the OP compound and thereby indicates the cumulative amount of an OP compound over a defined time period. The biosensor may be regenerated using a reagent to displace the OP compounds, e.g. flouride salts. Accuracy of the biosensor is assured if it is recalibrated prior to use.

These qualitative tests for the presence of OP compounds do not require an external source of energy or other equipment. However, the biosensor may comprise a carbon electrode for the detection of an OP compound by determining cholinesterase activity as indicated by $H_2O_2$. In this embodiment, the material, wherein the ChE is immobilized upon or within, is secured on the carbon electrode. In the instant invention, the biosensors may be stored for long periods of time at extreme temperatures and may also be used repeatedly.

A few examples of biosensor include test strips, badges and patches.

The following examples are intended to illustrate but not to limit the invention.

EXAMPLE 1

Determination of Possible Enzyme Interference

As polyether prepolymer derived from tolyl diisocyanate (TDI), reacts most favorably with free aliphatic amines such as lysine and arginine present on the surface of the ChEs (or any protein) to become a permanent cross-linked part of the material, computer aided molecular modeling of the enzymes was performed to highlight the available amino groups on the surface of each enzyme, and to determine whether the coupling of these groups to a porous support would interfere with enzymatic function. This may be performed on every enzyme for which its crystal structure is known, or enzymes which may be modeled by homology.

FIG. 1A illustrates the modeled surfaces of acetylcholinesterase, butyrycholinesterase and phosphotriesterase and shows the lysine and arginine residues on the surface of the ChEs which are available for coupling to the prepolymer. This was generated by Insight II, molecular modeling software, by Biosym Technologies. Based on the molecular modeling, there are at least one lysine and 29 arginine water-accessible residues on the surface of FBS-AChE to couple to the porous support, while 26 lysine and 26 arginine residues were modeled for equine-BChE. The majority of the lysine and arginine residues were found on the backside of the ChEs, and only a few are found on the side of the enzyme where the catalytic site gorge is located. The rim and the catalytic site gorge opening of both AChE and BChE appeared to be essentially devoid of lysine and arginine. Therefore, coupling these enzymes to the porous support should have minimal effect on the entrance of substrate, inhibitors such as OPs, or reactivators such as oximes which includes mono-disquartemary oximes, release of products of catalysis to and from the active site, and the kinetic rates of the enzymes. Similarly, a model of the surface of laccase (FIG. 1B) is shown with available residues to couple covalently to the prepolymer.

EXAMPLE 2

Synthesis of an Enzyme Bound Polyurethane Material

A typical synthesis of the material comprises mixing enzymes in phosphate buffer containing 1% (final concentration) surfactant with prepolymer. Polyether prepolymer derived from tolyl diisocyanate (TDI), Hypol prepolymer TDI 3000 (Hampshire Chemical, Lexington, Mass.), and Pluronic P-65 surfactant (BASF Specialty Chemicals, Parsippany, N.J.) were used. The 2-phase system is mixed and placed into a suitable mold and left to cure. FIG. 2 shows a cured material which comprises a sponge-like porous support. FIG. 12 shows a small material comprising immobilized AChE.

FIG. 3 schematically illustrates the specific reaction of the enzymes with prepolymer. Synthesis begins when $H_2O$ molecules react with the isocyanate groups present within the polyurethane prepolymer. Isocyanate reacts with the water to form an unstable carbonic acid, which degrades to an amine yielding $CO_2$. The $CO_2$ causes the polymer to rise and become porous, and simultaneously the amines readily react with the isocyanate groups leading to urea linkages.

Since the ChE contains amines that are on the surface and available to react with the isocyanate groups, they can become an integral part of the polyurethane support during synthesis. There is no significant entrapment of the enzyme in the material as found with cyclodextrins, or physical adsorption of the enzymes, as observed with activated carbon. The inclusion of a surfactant such as Pluronic P-65 at about 1% final concentration controls the final structure and absorption potential of the material.

To create a material comprising a porous polyurethane support, approximately 30 mL of 50 mM phosphate buffer, pH 8.0, containing P-65 surfactant buffer, was placed in a 600 mL plastic beaker. 3 to 5 mL of either purified FBS-AChE (7500 units) or purified Eq-BChE (5000 units) was added, followed by approximately 40 gm of Hypo 3000 prepolymer (tolyl diisocyanate). The two-phase system was mixed and the material was allowed to expand for 10 min, extruded from the container. The material was washed thoroughly with 50 mM phosphate buffer, pH 8.0, dried and stored in a zippered bag at 4° C. for future use.

EXAMPLE 3

Characteristics of Synthesized Material

Approximately 20–90% of the enzymes were covalently linked to the porous support through free amino- or hydroxyl groups. This was determined by the presence of enzyme in first and second washes of the material.

Since the enzymes can be attached at multiple points, they become a part of the cross-linked polymer support. The cross-linked polymer support imparts considerable stability to the bound enzymes. A large quantity of enzyme can be incorporated into a small polyurethane support, thereby rendering the cross-linked polymer support a highly stable and sensitive material for detection of OP compounds.

A. Enzymatic Activity

Five samples of materials containing FBS-AChE and five samples of materials containing Eq-BChE, ranging in weight from 1 to 40 mg, were suspended in 2.8 mL of 50 mM phosphate buffer, pH 8.0, and assayed using the method of Ellman. See Ellman, G. L., et al., (1961) *Biochem Pharmacol.* 7:88–95. A linear correlation was found between the weight of the sponge and enzyme activity for both FBS-AChE and Eq-BChE immobilizations. See FIGS. 16A and B. The linear correlation between the weight of the material and enzyme activity indicates a uniform immobilization of AChE or BChE throughout the material.

The material was washed with either 50 mM phosphate buffer, distilled water, or 10 mM ammonium bicarbonate without affecting substrate hydrolysis. Therefore, the mixing of prepolymer, surfactant, and enzyme in situ at 22° C. yields a useful and effective material retaining about 50% of the original activity of soluble ChE.

B. Protein Loading Capacity

The material has a significantly higher loading capacity for ChEs such as BChE or AChE. The final activity of the BChE immobilized in the material could be increased by adding larger quantities of enzyme during synthesis. See FIG. 4. When nonspecific protein (bovine serum albumin, BSA) was added to a constant amount of purified AChE, there was no reduction in ChE activity. See FIG. 5. Thus, higher potency materials may be synthesized with additional proteins, enzymes, and other ChEs. Additionally, materials effective for detecting a diverse array of OP compounds may be readily synthesized by with combinations of multiple enzymes or a plurality of enzymes.

C. Enzymatic Stability

As illustrated by FIG. 6, the immobilized ChE and OP hydrolase maintained enzymatic stability for more than 3 years at 4° C., more than 12 months at 25° C. and 45° C., respectively. If the material is frozen in liquid nitrogen, most of the original activity remains. TDI imparts remarkable stability to the immobilized ChE; about 50% of the original activity of the immobilized AchE and 20% of the activity of the immobilized BChE remained after 16 hours at 80° C., conditions under which the soluble enzymes would exhibit no activity. The ChE materials can be exhaustively dried under vacuum at 22° C. and then rehydrated without loss of enzyme activity. When AChE or BChE materials were exhaustively washed and assayed for activity, the wash and assay cycle repeated more than twenty times over three days, no decrease in activity occurred. See FIG. 7. This indicates that the material may be used repeatedly.

These results also demonstrate that the ChEs are covalently cross-linked in the porous support and that the ChEs will not leach out to skin, water, or equipment. Therefore, once the immobilized enzymes bind an OP compound the OP is removed from the surface requiring decontamination.

D. Kinetic Constants

The number of active sites of either the immobilized or soluble ChEs was determined by titration with the organophosphorous compound MEPQ, 7-(methylethoxyphosphinyloxy)- 1-methylquinolinium iodide. The bimolecular rate constants for the inhibition of AChE material and BChE material and the respective soluble enzymes by MEPQ at 25° C. showed that there was no significant difference between the soluble and covalently bound enzymes. See Table 1. These results demonstrate that the immobilized and soluble forms of ChEs interact with the OP compounds similarly. Therefore, enzymatic activity assays which are generally available and known in the art may be used.

An initial rates method using a modified Ellman's assay was used to determine the parameters $K_m$, $k_{cat}$, and $k_{cat}/K_m$ for immobilized and soluble AChE and BChE. The number of active sites of either the coupled or soluble ChEs was determined by titration with MEPQ. As shown in Table 2 and FIG. 8 for AChE, the $K_m$ values for the immobilized ChEs were about 10-fold greater than the corresponding soluble enzymes, and the $k_{cat}$ values were less dramatically affected. The combined effects on affinity for substrate and $k_{cat}$ resulted in approximately a 20 to 50-fold decrease in acylation ($k_{cat}/K_m$). Interestingly, while soluble BChE lacked substrate inhibition, immobilized BChE yielded substrate inhibition. These results suggest that covalent binding of surface residues of ChEs to the porous support changed some properties of the active site region of the bound enzymes directly or indirectly.

TABLE 2

Kinetic parameters for soluble and polyurethane coupled ChEs.

| Enzyme | Form | Substrate inhibition | $K_m$ (mM) | $K_{ss}$ (mM) | B | $K_{cat}$ (min$^{-1}$) | $K_{cat}/K_m$ (M$^{-1}$min$^{-1}$) |
|---|---|---|---|---|---|---|---|
| FBS-AChE | Soluble | yes | 0.119 | 18 | – | 2.8 × 10$^5$ | 2.5 × 10$^9$ |
|  | immobilized | yes | 1.090 | 22 | – | 5.9 × 10$^4$ | 5.4 × 10$^7$ |
| Equine-BChE | Soluble | no | 0.127 | 1.5 | 1.8 | 3.1 × 10$^4$ | 2.4 × 10$^8$ |
|  | immobilized | yes | 1.200 | 16 | – | 1.8 × 10$^4$ | 1.5 × 10$^7$ |

Determined in 50 mM phosphate, pH 8 at 25° C. using an initial rates method.
Calculated from $V_{max}$ and the active site concentration of ChE that was determined by MEPQ titration.
Values were calculated[2] using modified Haldane equations, and the special case where b = 0. The best fit between the two was determined using an F test, where significance was defined as $p < 0.05$.

$K_m$ Determination of Immobilized and Soluble Choline Oxidase

The $K_m$ of the soluble and immobilized forms (sponge) of choline oxidase are observed to be similar since there is little shift in the substrate curve, as shown by FIG. B, indicating that this enzyme is not only very suited to immobilization, but also for co-immobilization with the cholinesterates. The observed $K_m$ for soluble and sponge are 2.5 and 6.7 mM, respectively. See FIG. 19B.

E. pH of Soluble and Immobilized Enzymes

The pH profiles of immobilization and soluble AChE are identical and the enzymes exhibit activity through the broad pH range of 7–8.5. See FIG. 9. Since the pH profiles of soluble cholinesterases, choline oxidase and OP hydrolases have optimal activities in this same pH range, the materials may be optimized and diversified by employing a plurality of these multiple enzymes immobilization on or within a porous support.

pH of Soluble and Immobilized Enzymes as More Supporting Evidence

Figure 19A:
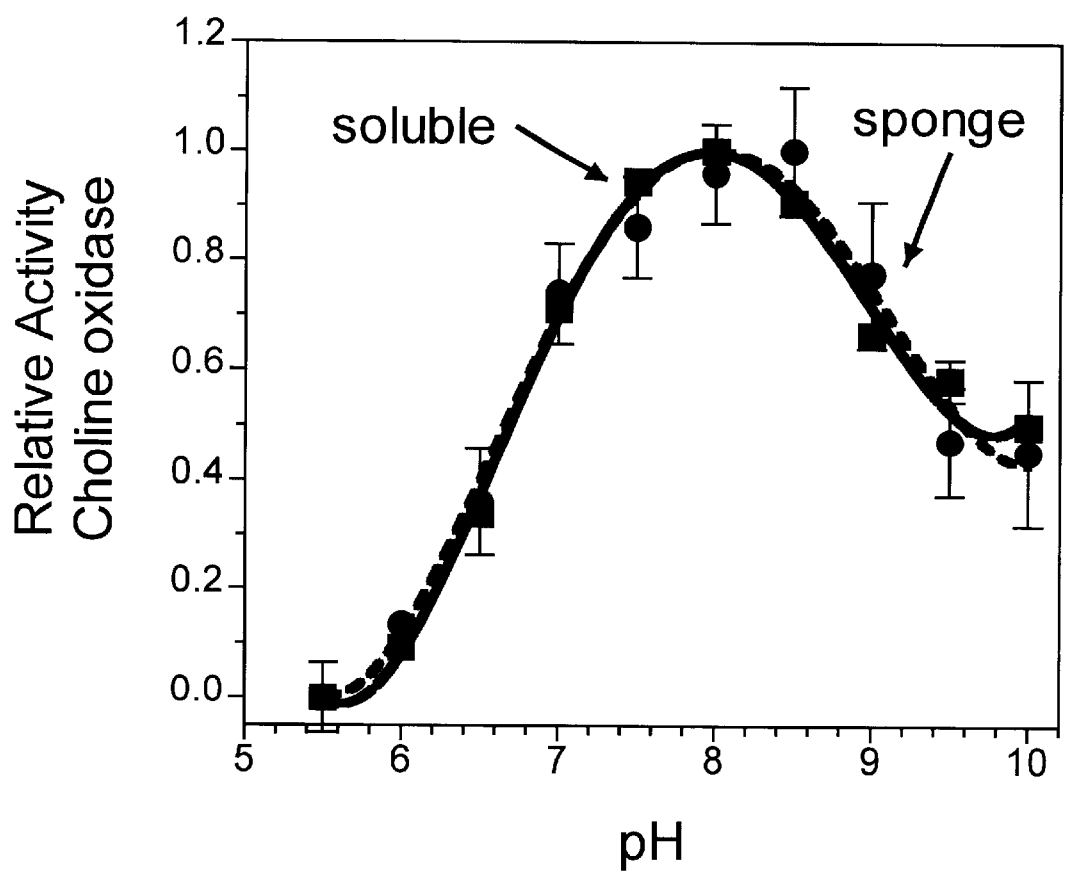
FIG. 19A shows the pH profile of soluble and immobilized choline oxidase.
Figure 19:
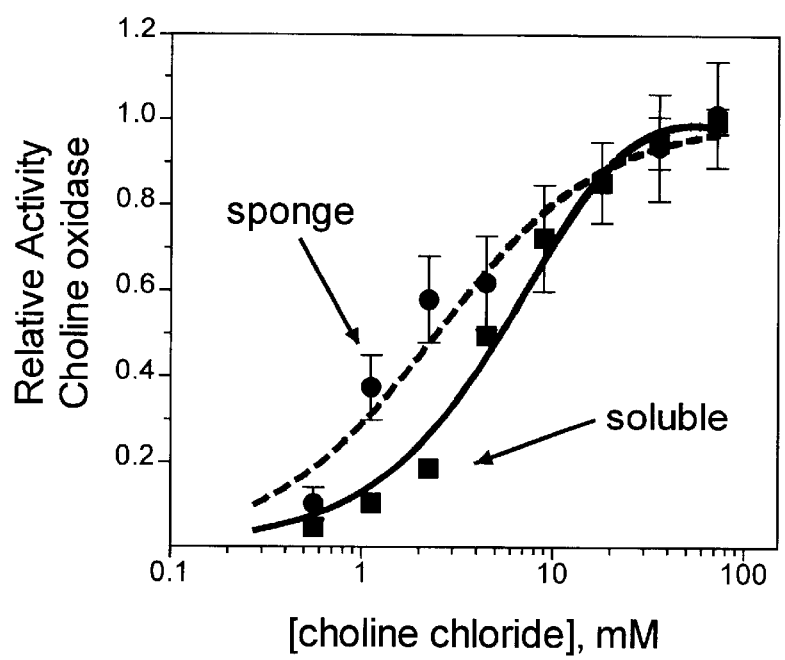
FIG. 19B shows the $K_m$ of the soluble and immobilized forms (sponge) of choline oxidase.

FIG. 19A: The pH profile of soluble and immobilized choline oxidase. Compare with FIG. 9, the pH profile of soluble and immobilized acetylcholinesterase.

Figure 20A:
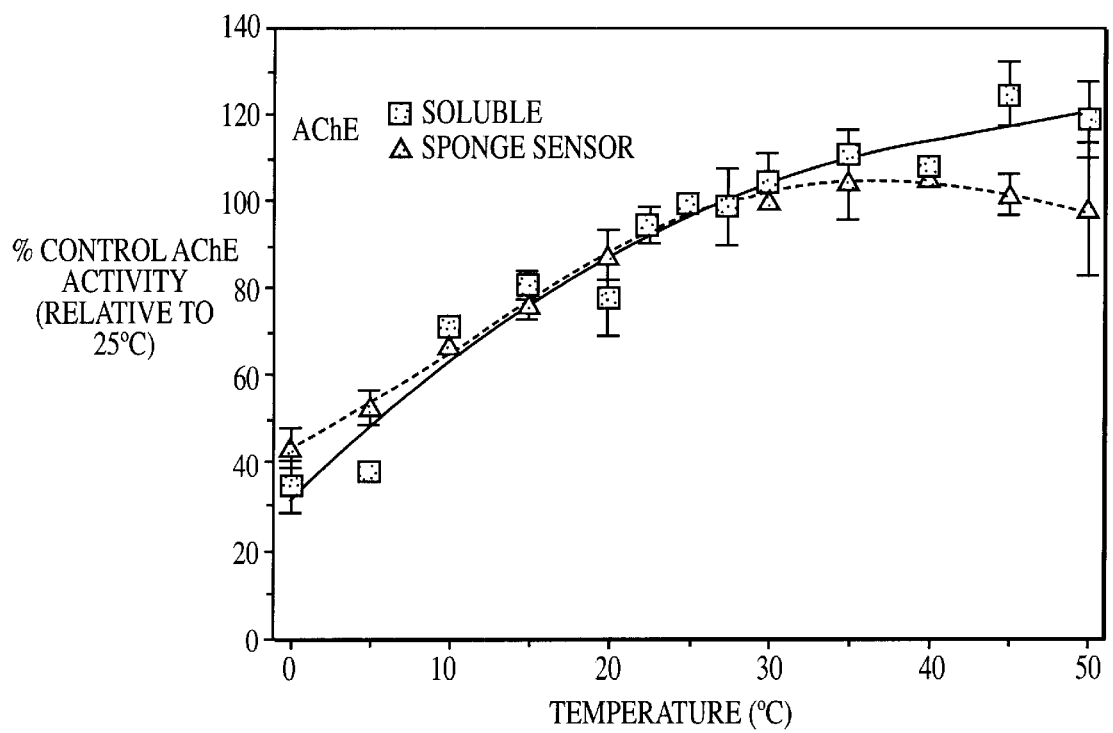
FIG. 20A shows The temperature profile of Immobilized and Soluble AChE.
Figure 20B:
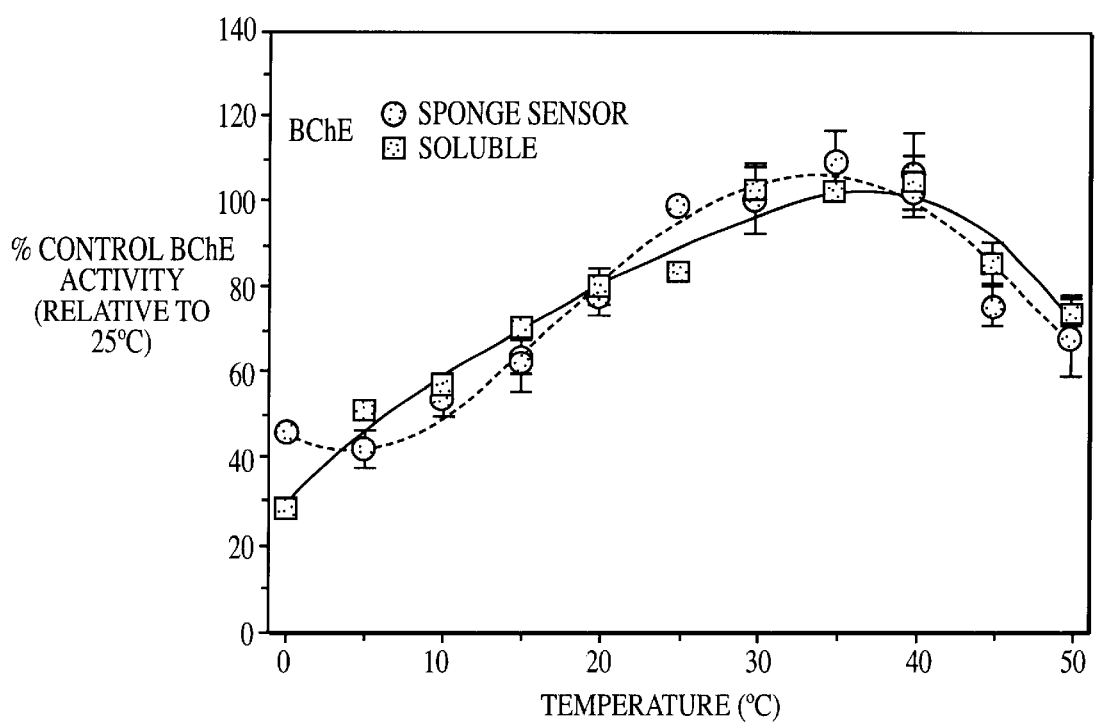
FIG. 20B shows the temperature profile of Immobilized and Soluble BChE.

F. Temperature Dependent Activity of Soluble Cholinesterases and Sensor (Immobilized) Cholinesterases The sensors containing immobilized AChE or BChE exhibited almost identical temperature dependent activity when compared to their soluble counterparts. However, as shown in FIG. 6, the immobilized enzymes are more resistant to the denaturing conditions of elevated temperatures for extended periods, while the soluble enzymes are not. The immobilized enzymes are also resistant to freezing in liquid nitrogen. These profiles indicate that at cold temperatures, the sensors could be warmed by body heat or an external source to increase the reaction rates. See FIGS. 20A and 20B.

EXAMPLE 4

Immobilization of a Plurality of Multiple Enzymes

ChEs were co-immobilized with bacterial OP hydrolase ($OPH_B$) and/or rabbit serum OP hydrolase ($OPH_R$). There was no reduction in the enzymes activities of AChE or BChE co-immobilized with OPH as compared to the enzymatic activities of each of these enzymes individually immobilized. See FIG. 10. Additionally, there was no reduction in the enzymatic activity of co-immobilized OPH. Therefore, a plurality of enzymes, which each enzyme differentially reacts with various OP compounds, may be selected and utilized in a material to create a decontamination material effective against a wide range of OP compounds.

Lastly, an example of multiple enzymes required for alternate detection schemes (see FIG. 13A) is also shown in FIG. 10. The co-immobilization of choline oxidase (Ch Ox) with AChE or BChE does not alter the immobilizing process or activity of the enzymes compared to the enzymes immobilized individually.

EXAMPLE 5

Rapid Mixing Synthesis

Figure 11A:
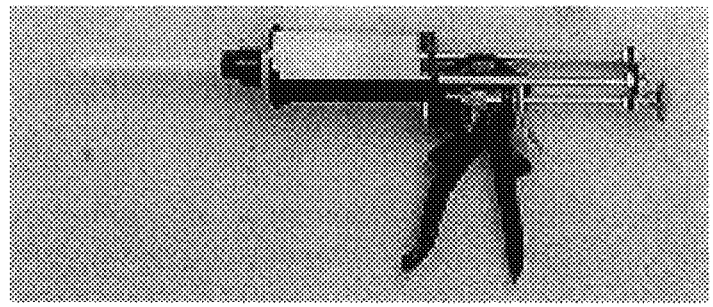
FIGS. 11A and 11B show a version of a manual mixing gun and a disposable mixing stator.
Figure 11B:
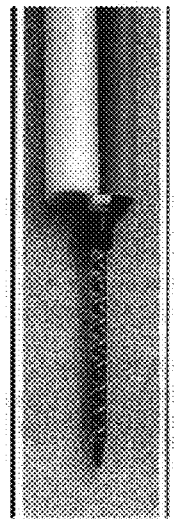

By utilizing a method of syntheses modified from the adhesive industry (CPA, Greenville, R.I. 02828) shear forces which decrease enzymatic activity are reduced. See FIG. 11. In this method, the enzyme is not in an organic buffer as required in some immobilization techniques. This results in less air-induced shearing, thereby maintaining enzymatic activity. This method is also simple to conduct, rapid and reproducible. The low shear mixing device more than doubles the resultant AChE and/or BChE immobilized enzyme activity when compared to an identical mixture prepared with the high shear device such as a mixing drill. See Table 3.

TABLE 3

| Technique | AChE Activity U/mg |
| --- | --- |
| High shear mixing drill | 0.100 |
| Low shear 2-chamber device | 0.270 |

EXAMPLE 6

Determination of Enzymatic Activity

FIG. 13 illustrates a variety of detection methods that may be employed with the biosensor of the present invention. Qualitative detection of the OP compounds may be visually performed by utilizing visible chromogens and/or chemiluminescent chromogens. Quantitative detection may be performed by using handheld devices, which measure amounts of fluorescence, chemiluminescence, or visible chromogens. In addition, an electronic biosensor comprising disposable carbon microelectrodes may be used to detect electrochemical signals from $H_2O_2$ generation.

The ChE activity of the materials were evaluated by using a modified Ellman method in an aqueous phosphate buffered environment containing either acetylthiocholine for AChE or butyrylthiocholine for BChE as substrates. The reactions, which produce an intense yellow color, were spectrophotometrically monitored at 412 nm. The final reaction product of the Ellman assay did not adsorb onto a material lacking ChE did not adsorb. The product generated was linear with time, thereby indicating that the release of the reaction product into the aqueous environment was not rate limiting. For determining the activity of the OP hydrolases, the substrate utilized was diethyl p-nitrophenylphosphate and the reactions were monitored at 500 nm.

The Ellman and OP hydrolase assays produce a yellow chromogen if the enzyme is not inhibited, and no color if the enzyme is inhibited. Alternatively, for cholinesterases, 2,6-dichloroindophenyl acetate (red color) turns blue (2,6 dichloroindophenylate) upon hydrolysis by ChE. Again, absence of a blue color indicates ChE inhibition by OP.

For fluorescent detection of ChE inhibition, the substrate may be either 1-methyl-7-acetoxyquinolinium iodide or fluorogenic maleimide N-(4-(7-diethylamino-4-methyl-coumarin-3-yl)phenyl)-maleimide. 1-methyl-7-acetoxyquinolinium iodide produces the highly fluorescent compound 1-methyl-7-hydroxyquinolinium iodide upon hydrolysis, i.e. 405 nm/ex 505nm emission. Fluorogenic maleimide N-(4-(7-diethylamino-4-methyl-coumarin-3-yl) phenyl)-maleimide condenses with the thiol formed from acetyl- or butyryl-thiocholine hydrolysis by ChEs, i.e. 390 nm/ex 473 nm emission.

For chemiluminescent detection, in addition to ChE and substrate (ACh or benzoylcholine), choline oxidase and peroxidase are added to a mixture containing luminol. In this chemiluminescent method, a light source is not needed, thereby allowing for a smaller, more energy efficient detectors. Additionally, chemiluminescent allows for detection with dark-adapted eyes. The indicator resorufin, a result of the reaction of Amplex Red (Molecular Probes, Inc.) and $H_2O_2$ has an advantage in that it is both flourescent, thereby yielding increased sensitivity, and is also a visible red chromogen (see FIG. 13).

For the typical Ellman colorimetric assay, the lower limit for detecting OP compounds by standard equipment is approximately 35 femtograms of OP. This limit may be obtained with a one $cm^2$ piece of material wherein ChE is immobilized upon or within. This amount may be increased or decreased during synthesis of the material. Thus, the maximum cumulative amount of OP nerve agent which will covalently bind to the material is about 100 pg. The lowest immediate detectable level (<1 min) may be as low as 5 pg.

Microelectrodes may be used to detect ChE activity. Thus, the in situ cross-linking scheme outlined above may be used with multiple enzymes, e.g., ChEs, choline oxidase, and peroxidase. This mixture is then spotted and cured about a carbon electrode. See FIG. 14. The enzyme-carbon electrode could be used to continuously analyze flowing liquids such as water without enzyme loss.

Optical analysis and common laboratory instrumentation such as UV-visible spectrophotometers, fluorometers, and electrochemical detectors may be used to develop a quantitative biosensor.

Similarly, the substrates and indicators above may be contained in small packets, liposomes or the like and embedded or incorporated within the porous support. When the material is squeezed, pressed or otherwise manipulated, the substrates and indicators are released and the resulting color change indicates the presence of an OP compound.

Determination of Enzymatic Activity

A 10 mg sponge containing immobilized choline oxidase and immobilized AChE was incubated in a cuvette containing 2.5 mL of buffer containing substrate (acetylcholine), indicator (Amplex Red from Molecular Probes, Inc), and horseradish peroxidase is outlined in FIG. 13B. One sponge was exposed to MEPQ at 25° C. for 5 min, rinsed in water and then placed in a second cuvette with the same buffer. Another cuvette contained only the above buffer but no biosensor sponge.

After a 5 min incubation at 25° C., the samples were observed visually, spectrophotometrically at 560 nm, and fluorometrically at 560 nm excitation and 580 nm emission. Visually against a white paper, the left sample (FIG. 13C) demonstrates the intense color (red) observed when the sensor active and reacts with the substrate. The middle sample, labeled B, depicts the state of the sensor after being exposed to the OP MEPQ—it is poisoned and no longer produces color. Indeed, it is indistinguishable for the sample on the right, labeled C, which contains only the buffer and no sensor.

The same sample could be monitored fluorometrically or in the visual range using handheld spectrophotometers. The advantage of fluorometric analysis is the significant enhanced sensitivity over analysis in the visual spectrum. Using laboratory spectrophotometers, there was a 4000-fold enhancement of the signal and sensitivity in the cuvettes when measured fluorometrically.

The AChE and choline oxidase sensor can be used to indicate the absence or presence of organophosphates in complete darkness without an energy source. The AChE/choline oxidase immobilized sensor was incubated in 2.5 mL of buffer containing substrate (acetylcholine), luminol (5-amino-2,3-dihydro-1,4-phthalazinedione), 10 ug/mL horseradish peroxidase. Luminescence was quantified in a fluorometer without excitation (no light source) and emission at 0 order (wide open to measure light that would be generated by an unpoisoned sensor reaction). The AChE hydrolyzes the substrate and the choline oxidase acts on the product (see the scheme in FIG. 13): the result is chemiluminescence. Chemiluminescence was observed for more than four minutes above the threshold of dark-adapted human eyes (indicated by the dotted horizontal line, see FIG. 13D).

EXAMPLE 7

Inhibition of Immobilized FBS-AChE with DFP 100 mg samples of immobilized FBS-AChE were incubated with varying concentrations of DFP in 2 mL of 50 mM phosphate buffer, pH 8.0, for 1 hour at 25° C. Residual DFP in the samples was measured by adding a 0.5 mL aliquot of the reaction mixture to 0.5 mL of a fresh 1 U/mL solution of FBS-AChE, incubating for 1 hour, and assaying 10 $\mu$l aliquots using the Ellman procedure. The results are shown in FIG. 17.

The inhibition of FBS-AChE activity by DFP was proportional to the stoichiometric amount of DFP added to the foam suspended in buffer.

EXAMPLE 8

Figure 18:
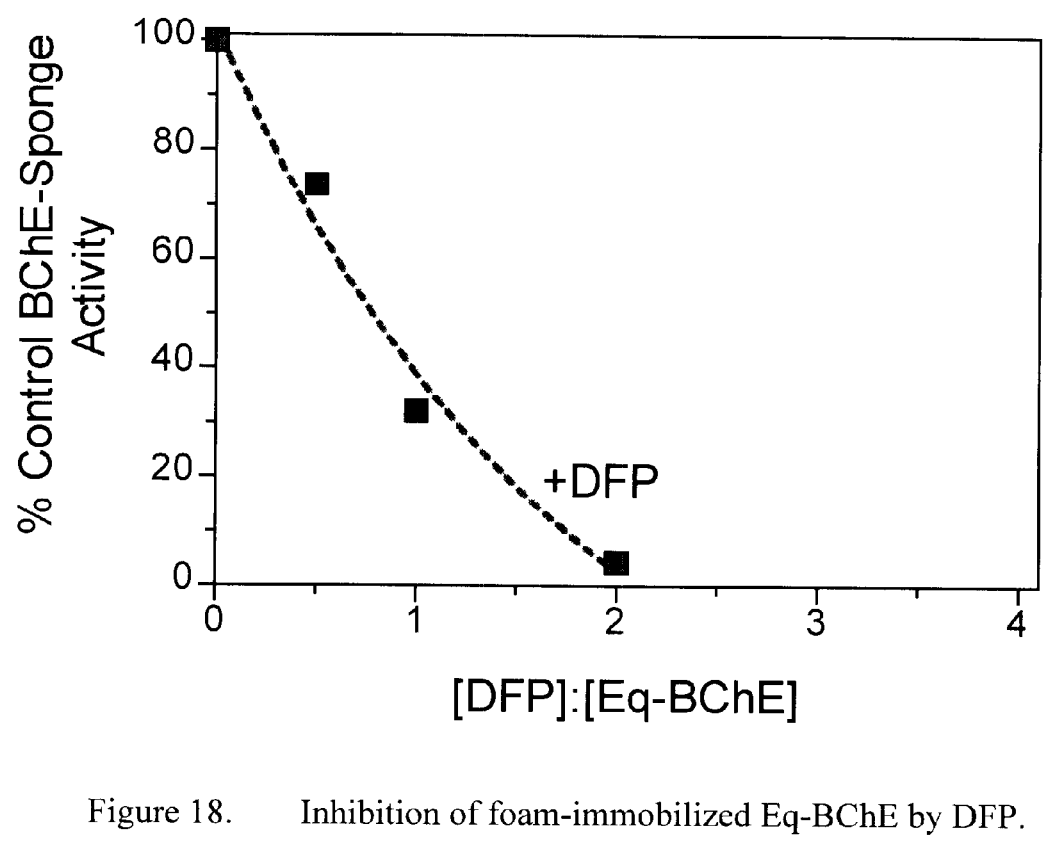

Inhibition of Immobilized Eq-BChE with DFP 50 mg samples of immobilized Eq-BChE were incubated with varying concentrations of DFP in 2 mL of 50 mM phosphate buffer, pH 8.0, for 18 hours at 25° C. Residual DFP in the samples was determined by adding a 0.5 mL aliquot of the reaction mixture to 0.5 mL of a fresh 1 U/mL solution of Eq-BChE, incubating for 1 hour, and assaying 10 $\mu$l aliquots using the Ellman procedure. The results are shown in FIG. 18.

EXAMPLE 9

Differential Biosensor Comprising Multiple Immobilized Enzymes

Materials comprising cholinesterases, OP hydrolases, and enzymes which hydrolyze other OPs may be covalently immobilized upon or within a porous support to form a differential biosensor. A differential biosensor could be made of various ChEs, OP hydrolases and/or laccases immobilized on or within a porous support, wherein each ChE, OP hydrolase and/or laccase is individually and separately secured onto a carrier such as a piece of plastic. For example, serum OP hydrolase from rabbit exhibits high activity with sarin, but not with soman. Therefore, a single piece of plastic whereupon a material having immobilized OPHr and a material having OP hydrolase from a source other than rabbit serum are secured, could act as a biosensor which differentiates between sarin and soman.

Additionally, since the enzymes from several species of halophilic and Alteromonas bacteria have considerable variation in enzymatic activity towards organophosphorous compounds, a plurality of materials wherein these enzymes are immobilized on or within the porous support may be separately secured on a carrier for use as a differentially acting biosensor. For example, since OPH from *A. undi* displays higher enzymatic activity against soman with respect to sarin and/or tabun, OPH from *A. undi* and OPH from another source could act as a biosensor which differentially detects soman over sarin and/or tabun. Additionally, the various OP hydrolases, ChEs, laccases and/or mediators of laccases and mutations thereof may be screened or developed for exhibiting different characteristic specificities and/or activities towards the a plurality of OP compounds.

Table 4 outlines a few enzymes that may be utilized for a rapid quantitative and qualitative identification of given OP compounds. The carrier could be divided into several compartments containing separate spots of immobilized enzymes that show different specificity for each OP. For example, if an OP agent is present in the sample tested, there would be inhibition AChE and/or BChE, i.e., no color change in the AChE and/or BChE compartments. If the OP agent is sarin, rabbit OP hydrolase would hydrolyze sarin and result in a color change in the rabbit OP hydrolase compartment. Additionally, the compartment containing *A. undina* would undergo a modest color change as there is only modest inhibition of the applied substrate since sarin is only a partial substrate. If VX is present, the color of the compartment containing laccase would be altered as laccase hydrolyzes VX.

TABLE 4

| OXYGEN PUMPING CELL | Relative activity of enzyme | | | |
|---|---|---|---|---|
| | AChE or BChE | Rabbit OPH | *Alteromonas undi* | Laccase |
| Sarin | Inhibited | ++ | + | – |
| Soman | Inhibited | – | +++ | – |
| Tabun | Inhibited | – | + | – |
| VX | Inhibited | – | – | ++ |

–not tested or not hydrolyzed

Thus, materials comprising immobilized enzymes such as those shown in Table 5 may be individually secured upon a carrier. After the carrier comprising the materials is exposed to the sample to be tested, the presence of particular OP agent may be determined by observing a color change of a given material in the presence of the appropriate substrate.

TABLE 5

Potential multiple immobilized enzymes

| Enzyme type and origin | Distinguishing characteristics | References |
|---|---|---|
| AChE, BChE | Inhibited by OPs | 1, 2 |
| Laccase | Hydrolyzes VX preferentially with mediator | 21 |
| OPH Human serum | Hydrolses tabun, VX poorly | 13 |
| Rabbit serum | Hydrolses sarin preferentially | 32 |
| Pseudomonas | Hydrolyses G agents | 33 |
| *Alteromonas undi* | Hydrolyses soman preferentially | 17 |
| Squid | Hydrotyses tabun, VX poorly | 34 |

EXAMPLE 10

Remote Quantitative and Qualitative Analysis of OP Compound

As an OP inhibited enzyme is not readily reversible and the enzyme is immobilized, the material may be transported from the test site to another site to be analyzed for the presence and amount of given OP compounds. Additionally, the material may be left at a site to monitor OP compounds for a period of time. Since the OP inhibited enzyme is not readily reversible, interfering compounds and compositions may be removed from the material either at the test site or at a different location. Furthermore, the analysis need not be conducted immediately or soon after sampling.

A. Fluoride-Induced Release of OP

High concentrations of $F^-$ cause the release of OP compound complexed to the inhibited ChE immobilized on the material. See FIG. 15. This results in a soluble phosphofluoridate, which is specific for the OP compound present. The phosphofluoridate may be identified and quantified by gas chromatography and further verified with mass spectrometry in order to determine the original OP compound. Specifically, a material containing the inhibited ChE and washed free of interfering compounds is acidified to pH 4 and incubated with 2M potassium fluoride. The solution is then extracted with a $C_{18}$ SepPak (Waters Associates, Milford, Mass.). The OP compound is eluted and identified by gas chromatography and mass spectrometry. Most of the OP agents of interest may be identified and discriminated from OP pesticides. In this example, the samples need not be frozen in order to be tested for OP compounds at a later date since the material is extremely resistant to mechanical stress, harsh chemical conditions, and extreme and varying temperatures.

B. Enzymatic Digestion

As an alternative procedure, enzymatic digestion may be used for post-exposure identification of OP compounds. The OP compounds may be released from the enzymes immobilized on or within the porous support and digested with 1M Tris buffer, pH 10, and alkaline phosphatase. Then the high molecular weight products may be concentrated, dissolved in a solution of pyridine and trimethylsilylation agents. The samples can then be analyzed by gas chromatography and mass spectrometry.

EXAMPLE 11

Enzyme Coupling Prior to Formation of the Material

The enzymes may be coupled together prior to formation of the material by means known in the art to form a cross-linked enzyme complex. See e.g. Hashida, S., Imagawa, M., Inoue, S., Ruan, K.-h, and Ishikawa, E. (1984) J. Applied Biochem. 6, 56–63 and Samaoszuk, M. K., Petersen, A., Lo-Hsueh, M., and Rietveld, C. (1989). (A peroxide-generating immunoconjugate directed to eosinophil peroxidase is cytotoxic to Hodgkin's disease cells in vitro.), Antibody Immunocon. Radiopharm. 2(1), 37–46.

For example, AChE may be conjugated to choline oxidase with one of the various cross-linkers and methods known in the art. Therefore, AChE and choline oxidase would be in close proximity so the product of AChE hydrolysis, choline, would fall right next to the choline oxidase to produce $H_2O_2$. This type of enzymatic cascade would provide more efficient coupling and a faster and more sensitive response. In addition, because of the proximity of choline oxidase, i.e. choline oxidase to AChE, the ratio of choline oxidase to AChE may be reduced. More than two different enzymes may be utilized.

The cross-linker utilized may be a multifunctional cross-linking agent. A wide variety of cross-linking agents are available from commercial suppliers, i.e. Pierce (Rockford, Ill.). These multifunctional cross-linking agents may comprise varying lengths of spacer arms to ensure that the bridge between the linked enzymes is an appropriate length for maintaining independent enzyme structure, function and activity. Typically, this would be a length of about 4–8 angstroms. However, the length may be up to 16 angstroms. Some cross-linking sites must be available for coupling the conjugated enzymes to the prepolymer. The cross-linking may be performed in the same buffer as used for the prepolymer reaction as explained in Example 2. The enzyme conjugate is then mixed with a prepolymer, as in Example 2, to form a polymeric material.

EXAMPLE 12

Long-term Sensing of Aqueous Environments for Organophosphates

A significant advantage of the immobilized enzymes is that they are covalent immobilized permanently within the polyurethane matrix. This affords the sensors with the following properties that are absent in the soluble state of the enzymes or when the enzymes are non-covalently attached to papers, tickets, or other indicating strips.

Figure 21A:
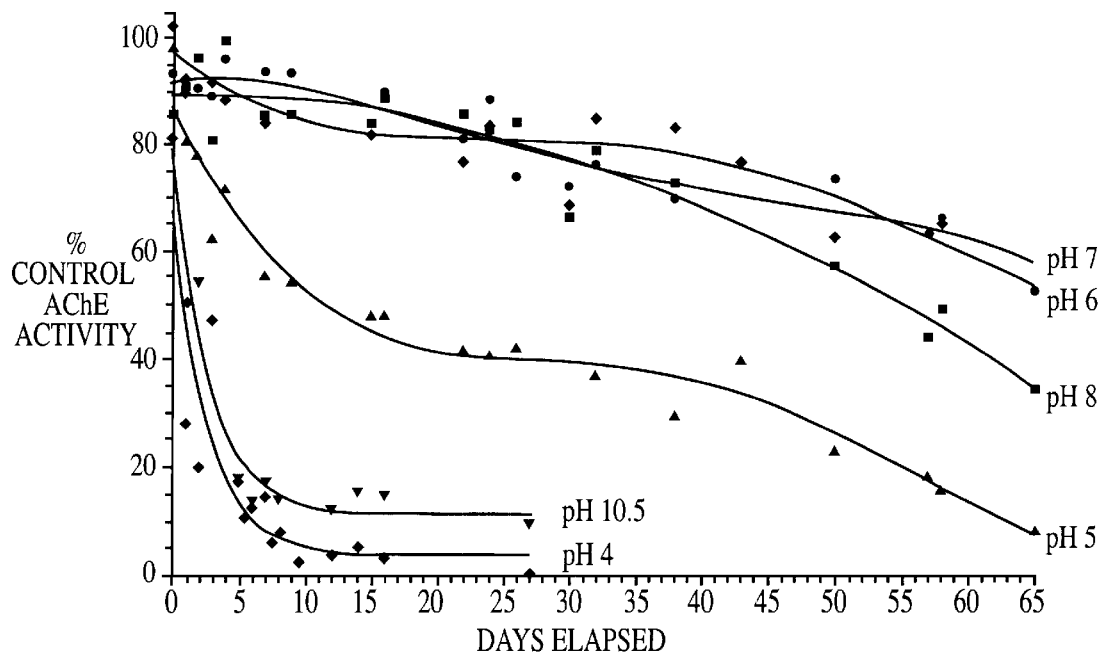
FIG. 21A shows AChE-sensor activities after continuous incubation at 25° C. at different pHs.
Figure 21B:
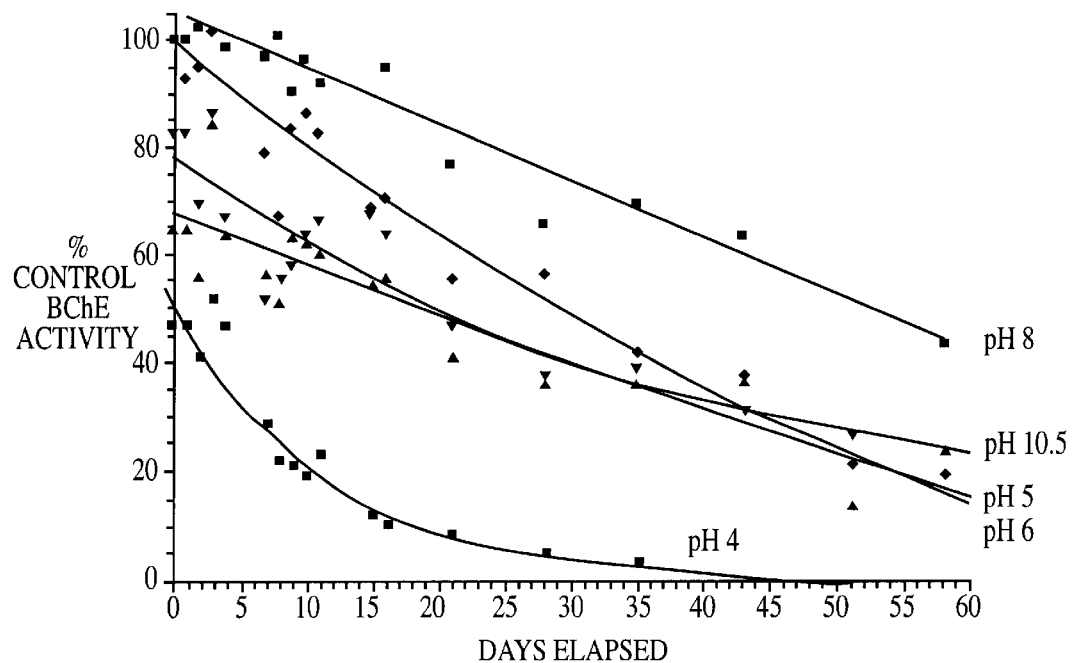
FIG. 21B shows BChE-sensor activities after continuous incubation at 25° C. at Different pHs.
Figure 21C:
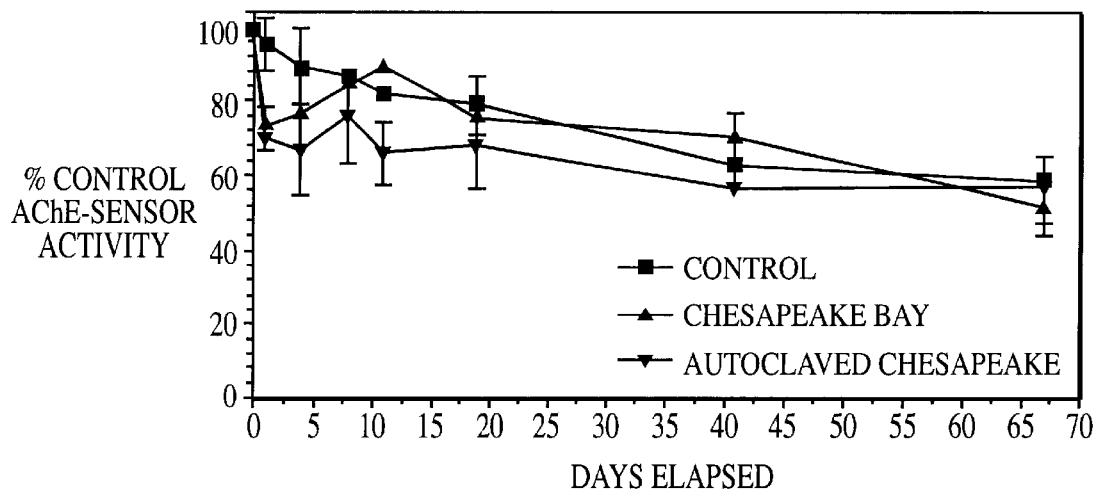
FIG. 21C shows AChE-sensor activity after continuous exposure to Chesapeake Bay (Brackish) Water at 25° C.

A. Ability to Retain Activity after Continuous Incubation at 25° C. at Different pHs The activity of immobilized AChE and BChE enzymes after 2 months at 25° C. in buffers at pHs from 4.0 to 10.5 are shown in FIGS. 21A and 21B, respectively. Even after more than a month in solution without sterilization, both ChE sensors retained most of their original activity at pHs between 6–8, and significant activity was only lost at the extremes of pH4 and 10.5. The loss of activity at the extreme pHs is not unexpected since it is known that these conditions cause irreversible denaturation of the soluble enzymes. However, note that for short periods of less than a few days, 50% or more of the original activity of the immobilized enzymes remained, while the soluble enzyme would have been completely denatured. These results demonstrate that the ChEs are suitable for long-term (days to many weeks) detection of OPs. For instance, the sensor could be left at a remote location and retrieved at a later date.

B. Ability to Retain Activity after Continuous Incubation in Natural Water Sources at Ambient (25° C.) Temperatures Additional evidence that the AChE sensor retains activity for extended periods in the environment is observed in FIG.

Figure 21D:
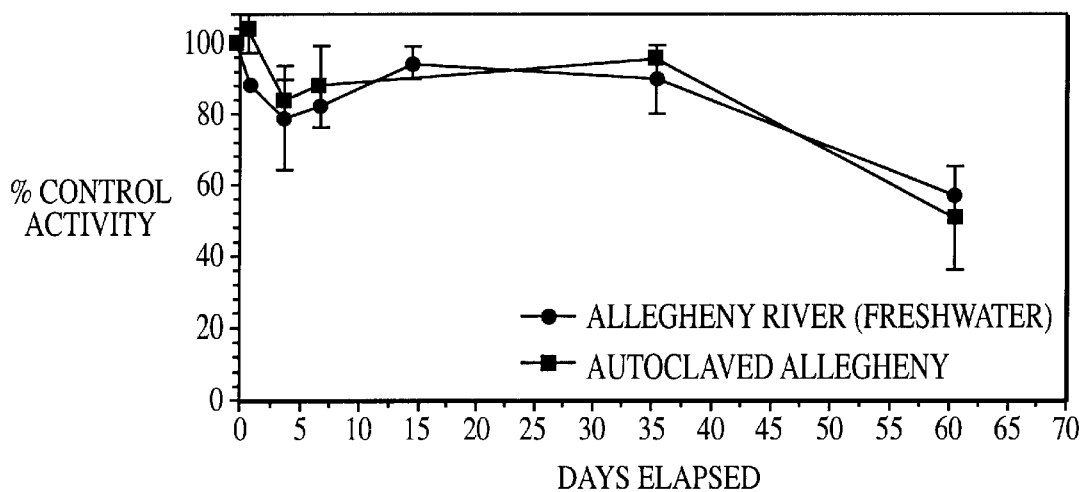
FIG. 21D shows AChE-sensor activity after continuous exposure to Allegheny River (Fresh) Water at 25° C.

21C (Exposure to Brackish Water, obtained from the Chesapeake Bay, Aberdeen, Md.) and FIG. 21D (Exposure to Fresh Water, obtained from the Allegheny River, PA). Most of the original activity of the sensor remains even when exposed to water for over 1 month. The immobilized enzyme was also resistant to natural microbiological flora and fauna that could degrade the enzyme since autoclaved water was not more stable than untreated water. Taken together, these results demonstrate the long-term sensing potential of these immobilized enzymes.

C. Comparison of the M272 Ticket with Example A and B, above

Figure 21E:
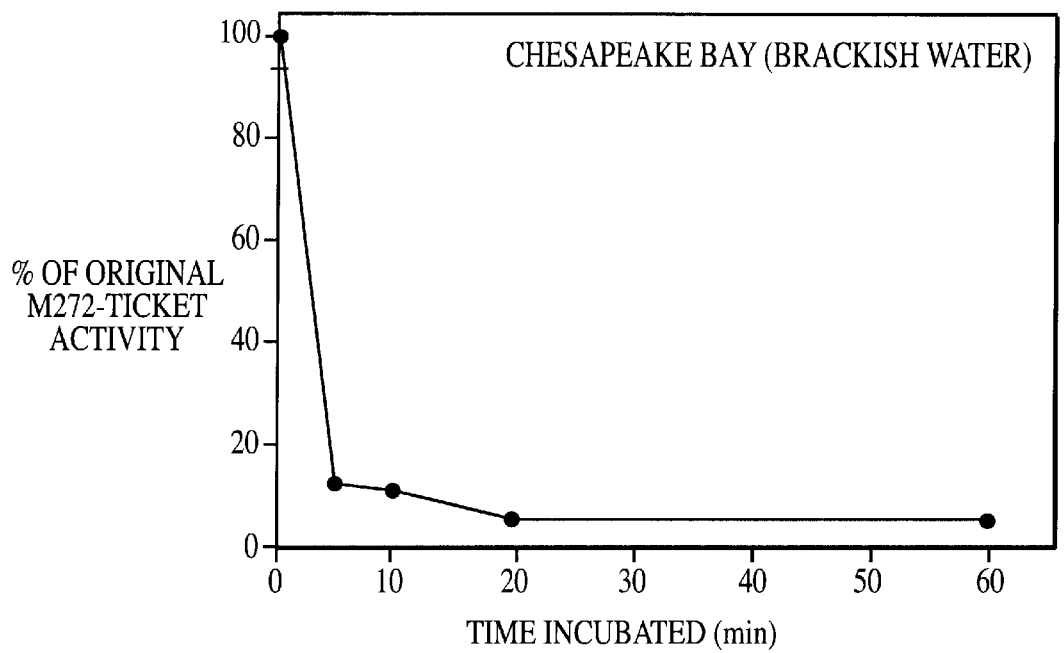
FIG. 21E shows sensitivity of M272 ticket to aqueous conditions (Chesapeake Bay brackish water).
Figure 21F:
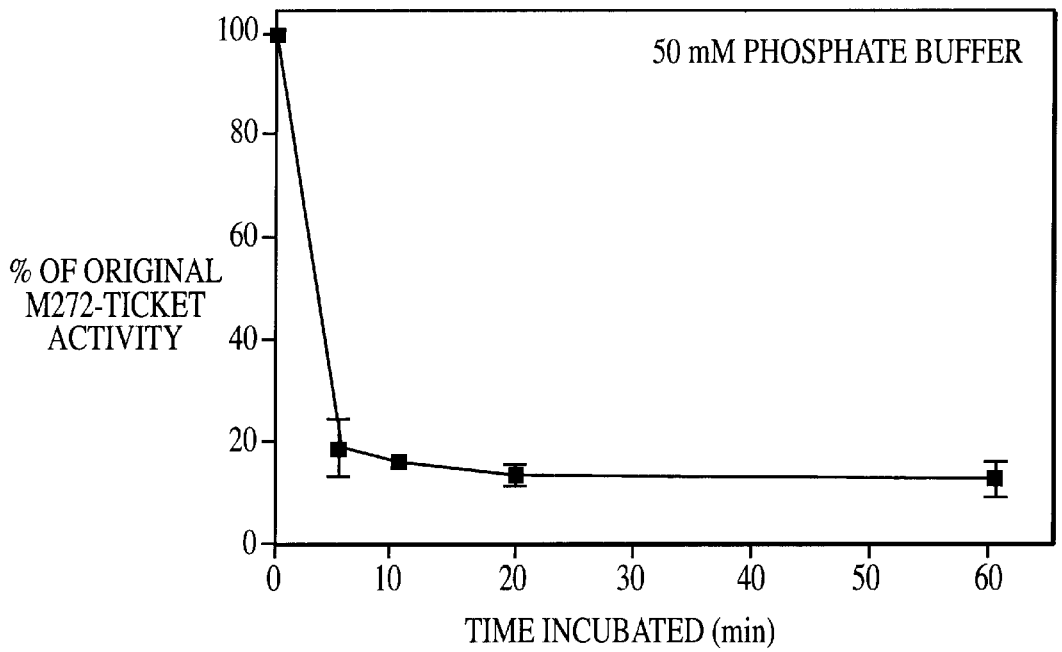
FIG. 21F shows sensitivity of M272 ticket to aqueous conditions (50 mM phosphate buffer, pH 8.0).

The M272 ticket is the currently fielded ticket for sensing organophosphates in aqueous solutions. The ticket contains non-covalently bound Eel cholinesterase. In contrast to the 1–2 months that the immobilized AChE and BChE sensors can retain activity even after continuous exposure to natural water sources, varying pH, temperature (up to years), etc, the M272 ticket looses more than 80% of its activity after exposure to Chesapeake Bay water (FIG. 21E) or a buffer (50 mM phosphate buffer, pH 8.0 (FIG. 21F) after only 5 minutes of exposure. Therefore, while the immobilized enzymes are suitable for long-term monitoring of the environment including water, in contrast, the M272 ticket is not suitable for even short-term monitoring of water sources for organophosphorus compounds.

EXAMPLE 13

Resistance to False Positives

Figure 22A:
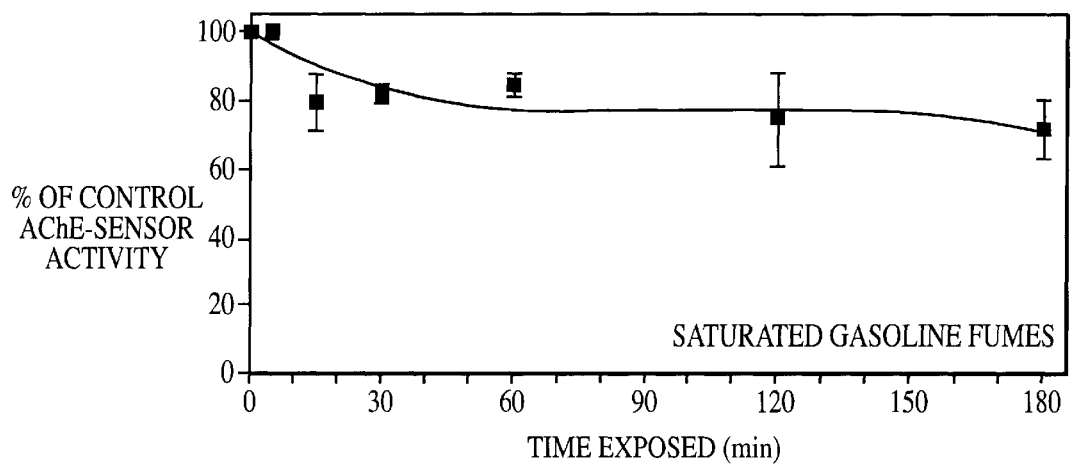
FIG. 22A shows AChE sensors are resistant to continuous exposure to saturated gasoline fumes and thus do not yield false positives.
Figure 22B:
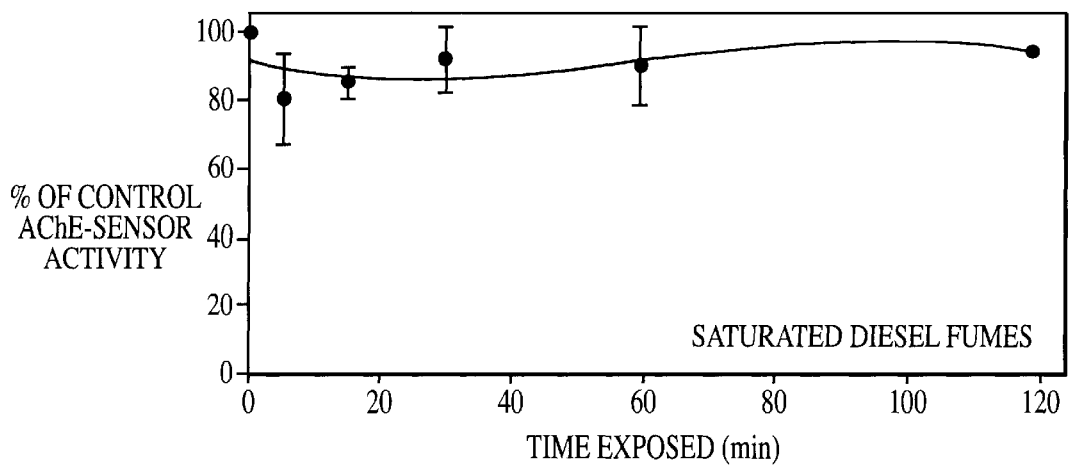
FIG. 22B shows AChE sensors are resistant to continuous exposure to saturated diesel fumes and thus do not yield false positives.

It is desirable to have a sensor resistant to false positives. In this definition, a false positive for OP would be any compound that denatures the enzyme. Since organic compounds are known to inhibit and denature many proteins and enzymes in their soluble form, the AChE sensor was evaluated for activity after exposure to saturated gasoline (FIG. 22A) and diesel fumes (FIG. 22B), conditions that could exist near fuel depots and machinery that are potential military or terrorist sites for attack with OPs. The immobilized enzymes retained more than 80% of their original activity after 2–3 hours of continuous exposure, and the polymer matrix showed no indication of breakdown. These results demonstrate that the matrix stabilized the immobilized acetylcholinesterase to denaturating conditions of the organic fuel vapors, thereby decreasing false positive responses.

EXAMPLE 14

Sensitivity of Soluble and Immobilized Mammalian AChE to Pesticide (Dichlorophos) and Organophosphate (Soman, GD)

Figure 23A:
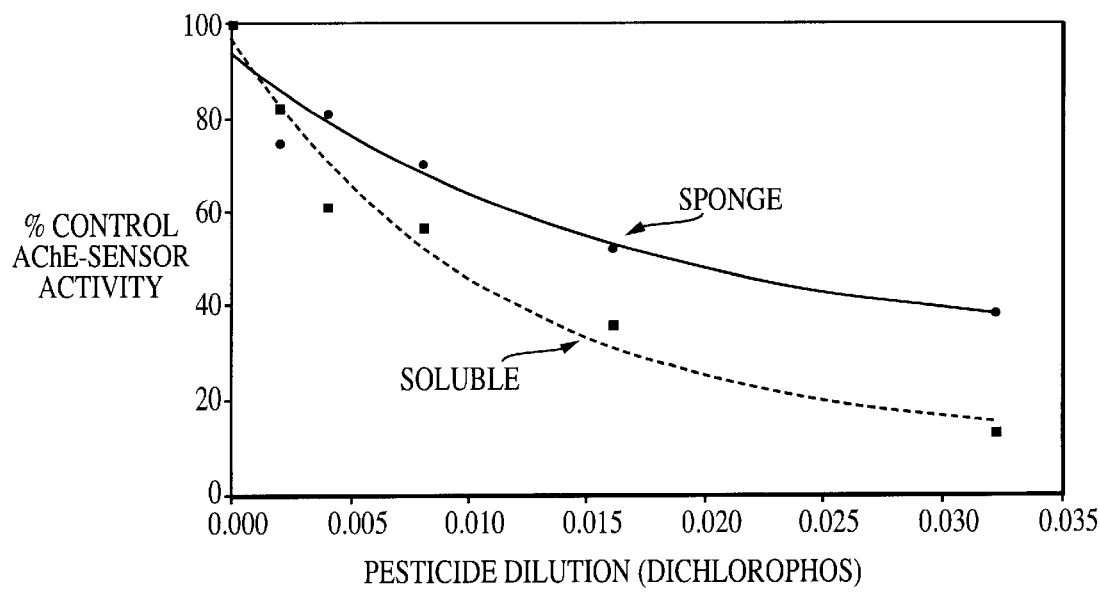
FIG. 23A shows dose-dependent inhibition of immobilized AChE sensor and soluble AChE to the pesticide dichlorophos.

AChE sensor and soluble AChE were exposed to dilutions of Dichlorophos in 2.5 mL of 50 mM phosphate buffer for 5 minutes, and then the activity of the enzymes in soluble form and immobilized sensor were determined. As shown in FIG. 23A, the sensitivity of the immobilized sensor and soluble enzyme exhibited very similar $EC_{50}$ values, however the slope for the sponge was about 20% less than the soluble enzyme. These results indicate that the AChE-sponge was slightly less sensitive to inhibition by the pesticide than the soluble mammalian enzyme.

Figure 23B:
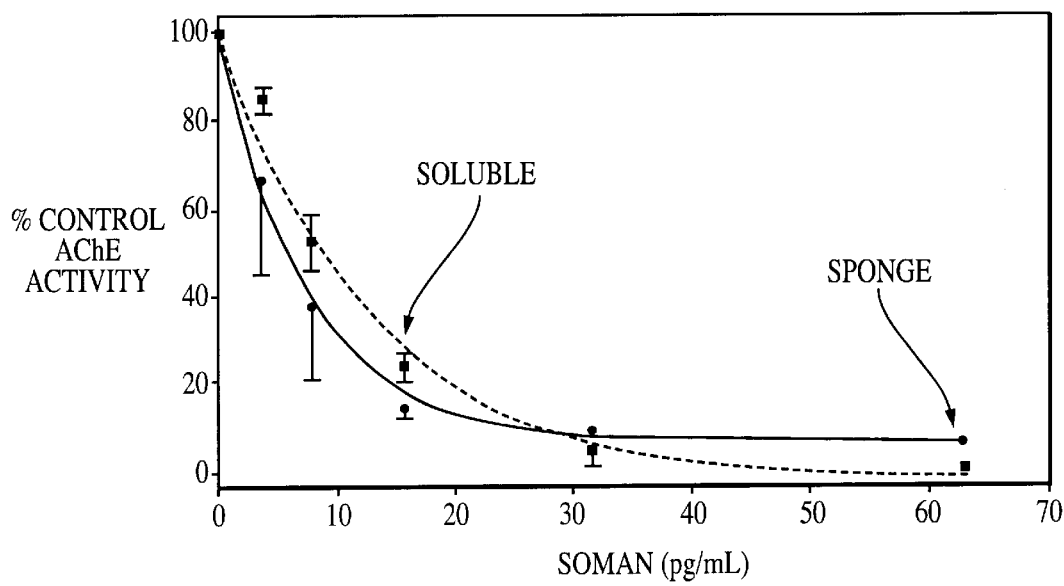
FIG. 23B shows dose-dependent inhibition of Immobilized AChE (sensor) and soluble AChE to the organophosphate soman (GD).

Similar results were observed for the inhibition of AChE sensor (immobilized enzyme) and the soluble acetylcholinesterase. FIG. 23B demonstrates that when the enzymes are exposed to soman for 5 minutes and then inhibition of the enzyme determined, the curves indicating loss of enzyme activity by soman exposure are not significantly different. Thus, in the absence of soman, there is color development and enzyme activity (100% level) while at 30 pg of soman, little color reaction develops and activity is less than 20% of the control level.

References Cited in Table 5

(17) DeFrank, J. J., Beaudry, W. T., Cheng, T-C., Harvey, S. P., Stroup, A. N., and Szafraniec, L. L. Screening of halophilic bacteria and Alteromonas species for organophosphorus hydrolyzing enzyme activity. Chem.-Biol. Interactions 87:141–148 (1993).

(33) Donarski W. J., Dumas D. P., Heitmeyer D. P., Lewis V. E., Raushel, F. M. Structure-activity relationships in the hydrolysis of substrates by the phosphotriesterase from *Pseudomonas diminuta*. Biochemistry 28:4650–5 (1989).

(32) Furlong, C. E., Richter, R. J., Chapline, C. and Crabb, J. W. Purification of rabbit and human serum paraoxonase. Biochemistry, 30:19133–10140 (1991).

(13) Gan, K. N., Smolen, A., Eckerson, H. W., La Du, B. N. Purification of human serum paraoxonase/arylesterase. Evidence for one esterase catalyzing both activities. Drug. Metab. Disp. 19:100–106 (1991).

(34) Hoskin, F. C., Roush, A. H. Hydrolysis of nerve gas by squid-type diisopropyl phosphorofluoridate hydrolyzing enzyme on agarose resin. Science 215:1255–7 (1982).

(2) Maxwell, D. M., C. A. Castro, D. M. De La Hoz, M. K. Gentry, M. B. Gold, R. P. Solana, A. D. Wolfe, B. P. Doctor. Protection of rhesus monkeys against soman and prevention of performance decrement by treatment with acetylcholinesterase, Toxicol. Appl. Pharmacol. 115 44–49 91992).

(21) Personal Communication, Dr. Gabriel Amitai, Israel Institute for Biological Research, Ness Ziona, Israel. (1) Taylor, P., Anticholinesterase agents, in: A. G. Gilman, T. W. Rall, A. S. Nies, P. Taylor (Eds.), The Pharmacological Basis of Therapeutics, Pergamon, New York, pp. 131–149 (1990).

Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. A biosensor for analyzing a sample for at least one organophosphorous and/or an organsulfur compound comprising at least one enzyme immobilized on or within a foam support by covalent bonds, wherein the enzyme is selected from the group consisting of: acetylcholinesterase (AChE), butyrylcholinesterase (BChE), triesterase, pseudocholinesterase, choline oxidase, peroxidase, organophosphate hydrolase (OPH), phosphotriesterase and paraoxonase and wherein the organophosphorous and/or organosulfur compounds are inhibitors of one or more of the enzymes.

2. The biosensor of claim 1, further comprises multiple zones wherein each zone contains an individual enzyme which is selected to differentiate between one or more of the organophosphorous and or organosulfur compond types.

3. The biosensor of claim 2, wherein the multiple zones form an array.

4. The biosensor of claim 1, wherein the biosensors are suitable for measuring for detecting organophosphorous and/or organosulfur compound(s) in gasses, and liquids and on solids.

5. The biosensor of claim 1, wherein the detection is based on the inhibition of cholinesterase activity.

6. The biosensor of claim 1 further comprising a carbon electrode for the detection of the organophosphorous and/or an organosulfur compound by measuring cholinesterase activity.

7. The biosensor of claim 1, wherein the foam is urethane.

8. The biosensor of claim 7, wherein the foam is synthesized from a reaction of a urethane, polyether or polyester polyol with isocyantates in the presence of crosslinking agents.

9. The biosensor of claim 8, wherein the foam is synthesized in the presence of the enzyme.

10. The biosensor of claim 9, wherein the enzyme is incorporated into the foam structure.

11. The biosensor of claim 8, wherein the synthesis is a rapid mixing one.

12. The biosensor of claim 1, wherin the foam support is secured upon a carrier.

13. The biosensor of claim 1, wherein the enzyme, a first enzyme, is coimmobilized with or conjugated to an enzyme, a second enzyme, that reacts with a product produced by the first enzyme or with OP.

14. The biosensor of claim 13, wherein the first enzyme is a cholinesterase and the second enzyme is choline oxidase.

15. The biosensor of claim 13, wherein the first enzyme is a cholinesterase and the second enzyme is OP hydrolase.

16. The biosensor of claim 1, wherein the presence of the enzyme is measured by its activity.

17. The biosensor of claim 16, wherein activity is detected by an indicator for fluorescent, chemiluminescent or visible chromogen detection.

18. The biosensor of claim 16, wherein the activity is determined based on an enzymatic substrate selected from acetylcholine, butyrylthiocholine, diethyl p-nitrophenylphosphate, 2,6-dichloroindophenyl acetate, 1-methyl-7-acetoxyquinolinium iodide, n-(4-(7-diethylamino-4methyl-coumarin-3-yl)phenyl)-maleimide or other known substrates of cholinesterases.

19. A method for detecting and measuring at least one hazardous chemical in a sample comprising contacting the biosensor of claim 1 with a sample and detecting and/or measuring the hazardous chemical.

20. The method of claim 19 further comprising applying an indicator for visually, chemically and/or electrically detecting and measuring a hazardous chemical wherein a visual, chemical and/or electrical change in the presence of said indicator indicates the presence and amount of the hazardous chemical.

21. The method of claim 19, wherein the contacting step and the detecting step are not perfomed immediately after the other.

22. The method of claim 19, wherein the hazardous chemical is OP and the detecting and/or measuring occurs after the OP is released from the enzyme.

23. The method of claim 22, wherein the OP is released by contacting the enzyme with a flourine anion and the detecting and measuring step involves the separation of OP and its measurement.

24. A method of making a biosensor for detecting and measuring a hazardous compound comprising immobilizing a plurality of enzymes or a cross-linked enzyme complex on, within or encapsulated in a porous support wherein the plurality of enzymes or the a cross-linked enzyme complex comprises at least one enzyme selected from the group consisting of:

acetylcholinesterase (AChE), butyrylcholinesterase (BChE), triesterase, pseudocholinesterase, choline oxidase, peroxidase, organophosphate hydrolase (OPH), phosphotriesterase, paraoxonase, laccase, mediators of laccase, cofactors of laccase and ABTS.

25. The method of claim 24 wherein the step of immobilizing comprises mixing said plurality or said cross-linked enzyme complex with a polyurethane prepolymer.

26. The method of claim 25 wherein said polyurethane prepolymer comprises a mixture of at least one diisocyanate.

27. The method of claim 26 wherein the diisocyanate is tolyl diisocyanate.

28. The method of claim 25 wherein equal parts of said plurality or said cross-linked enzyme complex and said polyurethane prepolymer are simultaneously mixed under conditions which fold the plurality of enzymes or said cross-linked enzyme complex with the prepolymer.

29. The method of claim 27 wherein the mixing is done with a static mixing stator.

30. A kit for detecting and measuring at least one hazardous chemical in a sample comprising the biosensor of claim 1 and reagents for visually, chemically and/or electrically detecting and measuring the hazardous chemical.

31. The kit of claim 30 further including a means for transmitting results to a central collection point.

* * * * *

UNITED STATES PATENT AND TRADEMARK OFFICE
CERTIFICATE OF CORRECTION

PATENT NO.    : 6,406,876 B1
DATED         : June 18, 2002
INVENTOR(S)   : Richard K. Gordon and Bhupendra P. Doctor It is certified that error appears in the above-identified patent and that said Letters Patent is hereby corrected as shown below:

<u>Title page,</u>
Item [54], Title should read -- IMMOBILIZED ENZYMES AS BIOSENSORS FOR CHEMICAL TOXINS --

Item [75], Inventors, should read --Richard K. Gordon, Potomac, MD (US)
Bhupendra P. Doctor, Potomac, MD (US) --

Related U.S. Data, please insert -- Provisional application 60/130,989 filed April 26, 1999 --

Signed and Sealed this

Twelfth Day of November, 2002

Attest:

Attesting Officer

JAMES E. ROGAN
Director of the United States Patent and Trademark Office